(12) United States Patent
Schraft et al.

(10) Patent No.: US 6,712,828 B2
(45) Date of Patent: Mar. 30, 2004

(54) DEVICE AND PROCEDURE FOR JOINING HOLLOW ORGANS

(75) Inventors: Rolf Dieter Schraft, Stuttgart (DE); Andrea Hiller, Stuttgart (DE); Jochen Klenk, Murrhardt (DE); Joachim-Gerd Rein, Korntal (DE); Alexander Paul Horke, Bietigheim-Bissingen (DE)

(73) Assignee: Fraunhofer-Gesellschaft zur Forderung der Angewandten Forschung, E.V. (DE)

( * ) Notice: Subject to any disclaimer, the term of this patent is extended or adjusted under 35 U.S.C. 154(b) by 133 days.

(21) Appl. No.: 09/835,207

(22) Filed: Apr. 13, 2001

(65) Prior Publication Data

US 2002/0055752 A1 May 9, 2002

Related U.S. Application Data

(63) Continuation-in-part of application No. 09/747,628, filed on May 25, 2001.

(30) Foreign Application Priority Data

Nov. 9, 2000 (DE) .......................................... 100 55 472
Apr. 11, 2001 (DE) .......................................... 101 18 138

(51) Int. Cl.[7] .............................................. A61B 17/04
(52) U.S. Cl. ...................................... 606/144; 606/153
(58) Field of Search ................................ 606/153, 139, 606/144, 145, 146, 147

(56) References Cited

U.S. PATENT DOCUMENTS

| | | | | |
|---|---|---|---|---|
| 4,930,674 A | | 6/1990 | Barak | |
| 5,285,945 A | | 2/1994 | Brinkerhoff et al. | |
| 5,320,632 A | * | 6/1994 | Heidmueller | 606/144 |
| 5,403,329 A | * | 4/1995 | Hinchcliffe | 606/147 |
| 5,554,162 A | * | 9/1996 | DeLange | 606/153 |
| 5,626,588 A | * | 5/1997 | Sauer et al. | 606/144 |
| 5,732,872 A | | 3/1998 | Bolduc et al. | |
| 5,779,719 A | * | 7/1998 | Klein et al. | 606/144 |
| 5,964,773 A | * | 10/1999 | Greenstein | 606/148 |
| 6,358,258 B1 | * | 3/2002 | Arcia et al. | 606/139 |
| 2002/0077636 A1 | * | 6/2002 | Arcia et al. | 606/153 |

FOREIGN PATENT DOCUMENTS

| | | |
|---|---|---|
| DE | 4137218 | 2/1993 |
| WO | WO9/940851 | 8/1999 |
| WO | WO/0059382 | 10/2000 |

* cited by examiner

*Primary Examiner*—Todd E. Manahan
(74) *Attorney, Agent, or Firm*—Young & Basile, P.C.

(57) ABSTRACT

The invention relates to a device for joining hollow organs with an elongated holder and a needle carrier which is positioned at one end of the holder, where the needle seat extends radially, forming an overhang projecting beyond the periphery of the holder, as well as with a plurality of needles which are disposed standing vertically on the projecting overhang of the needle seat, surrounding the holder.

32 Claims, 28 Drawing Sheets

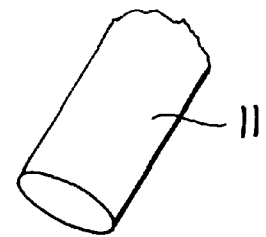
FIG.1A
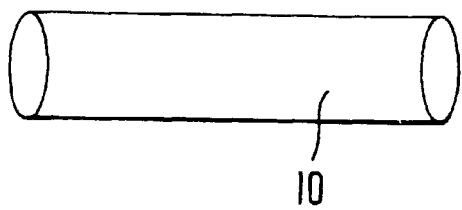
FIG.1B
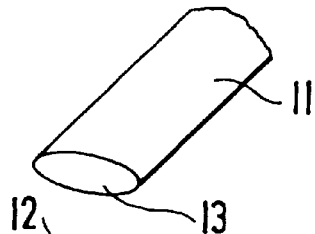
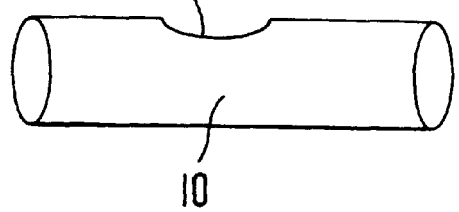
FIG.1C
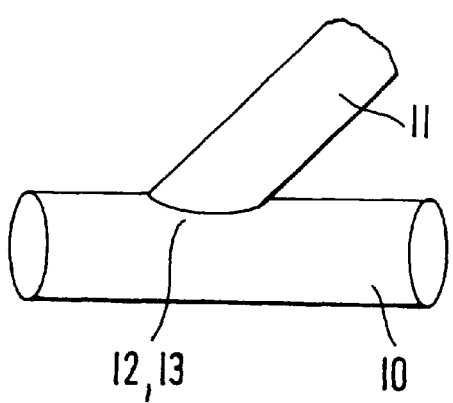

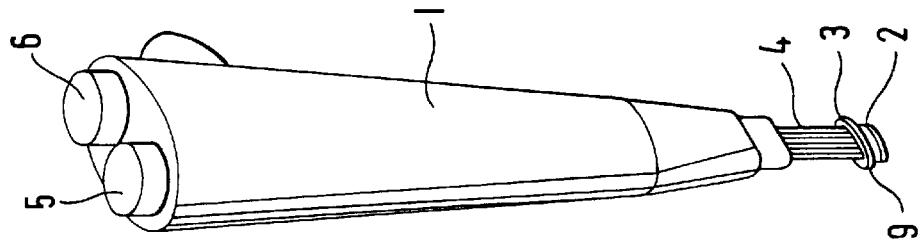
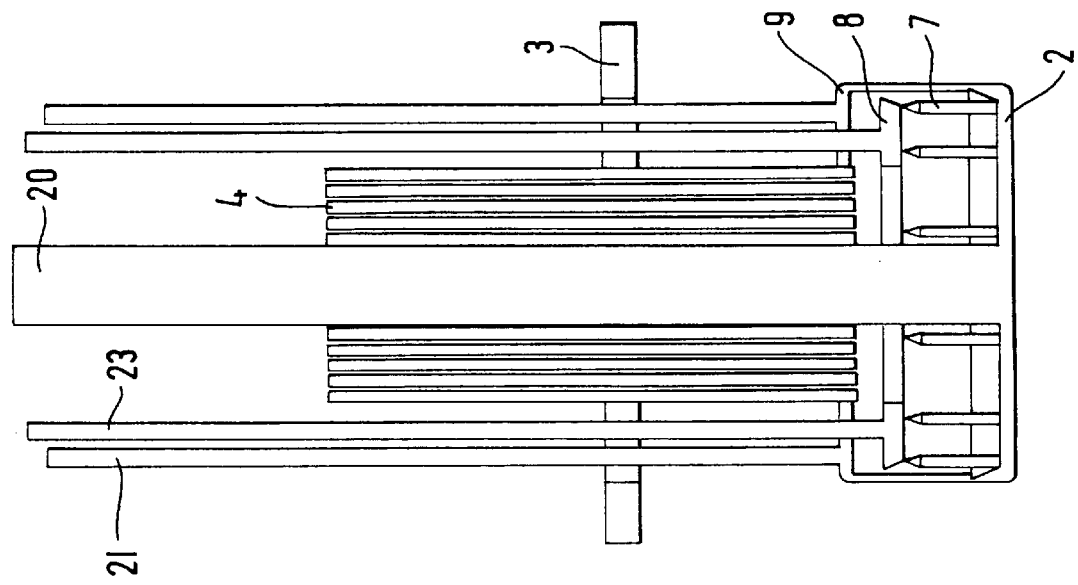
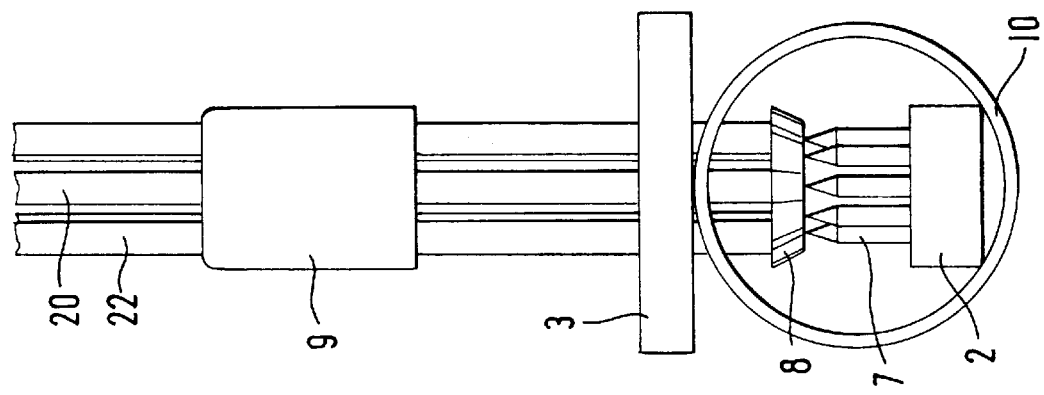

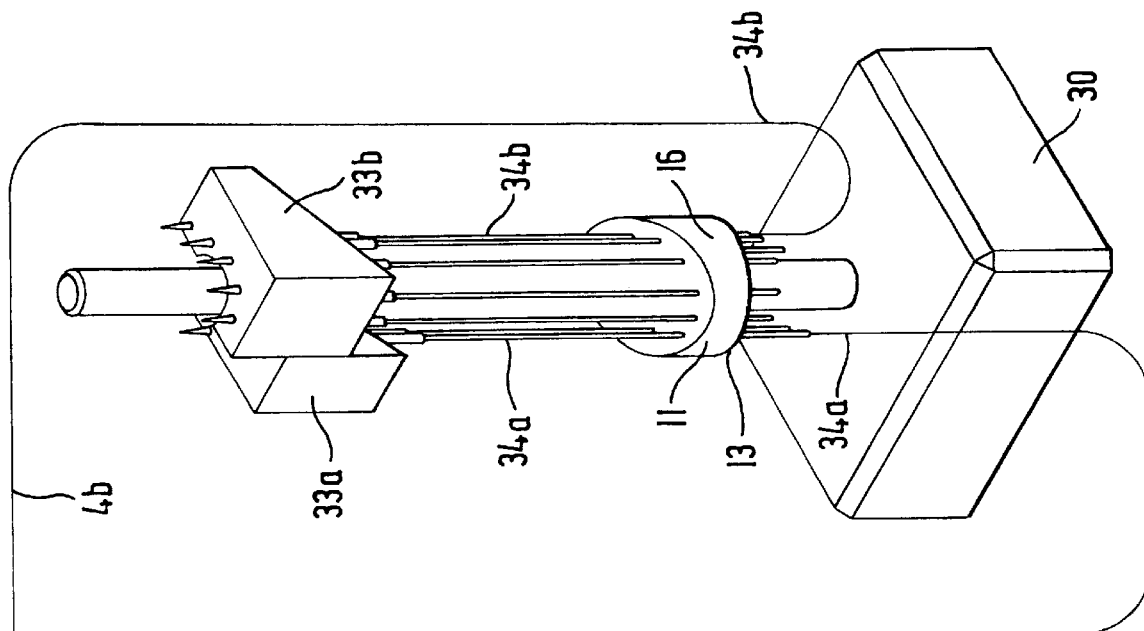
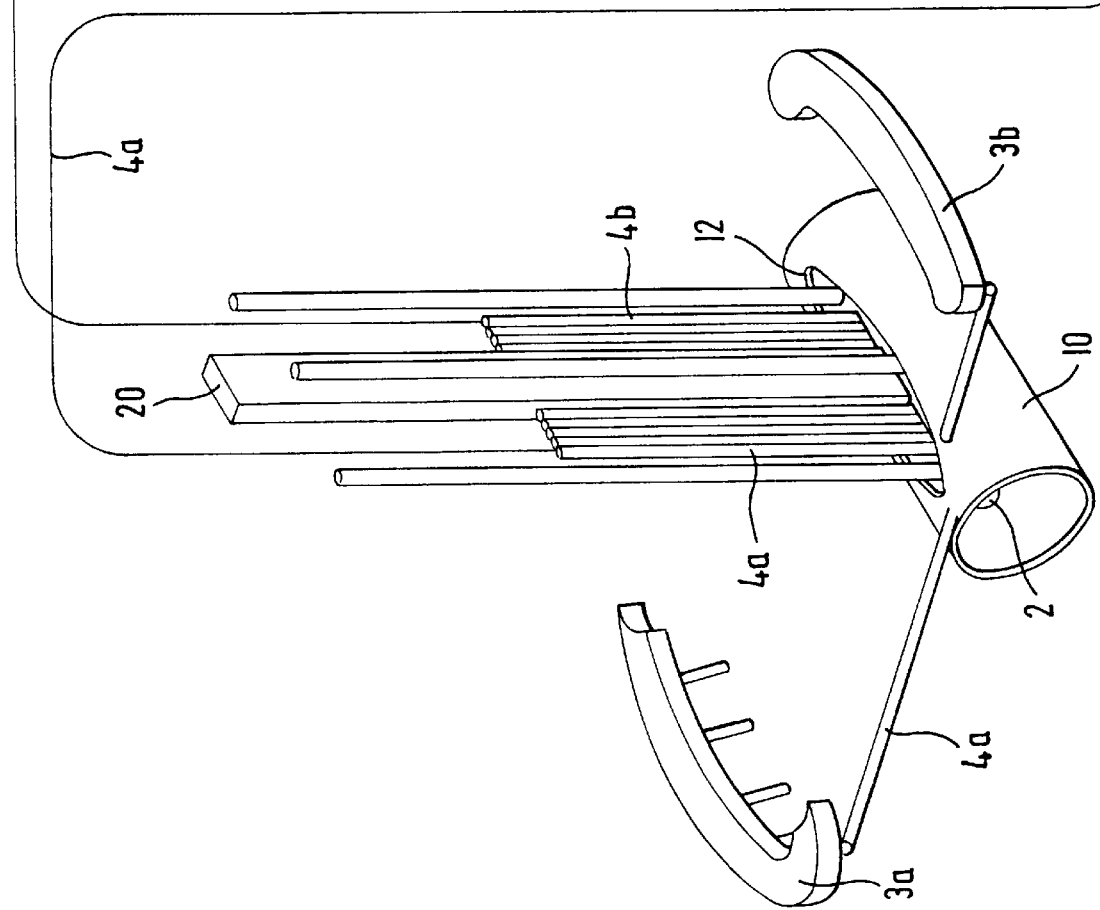
FIG. 16

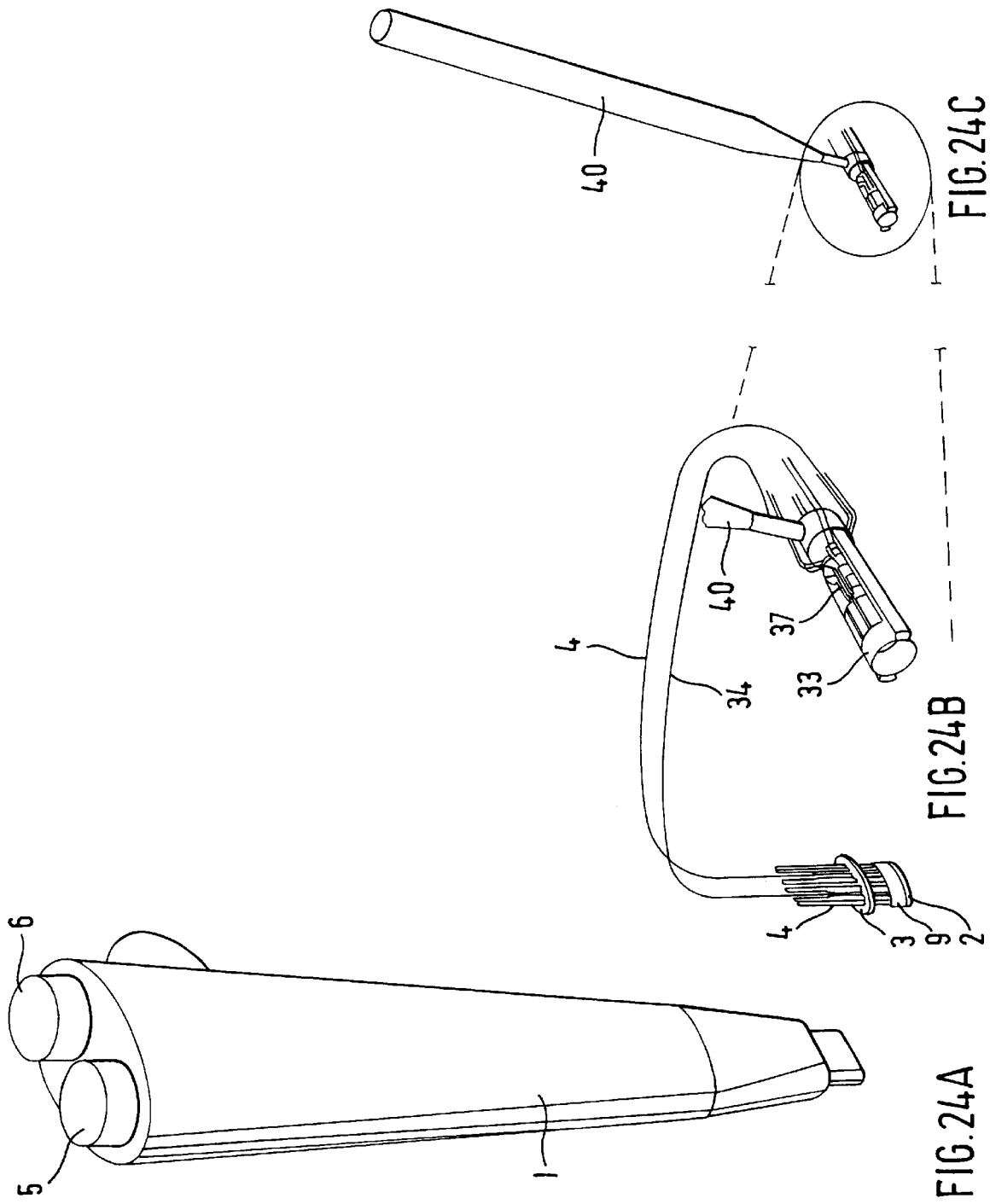

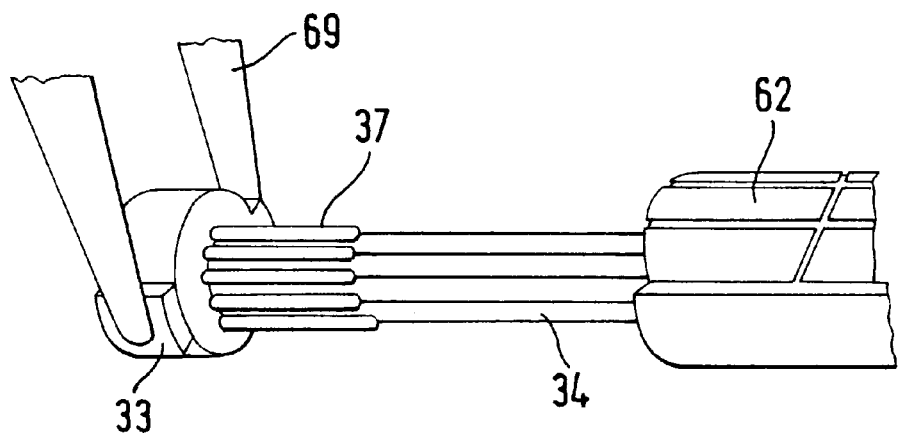
FIG. 27G
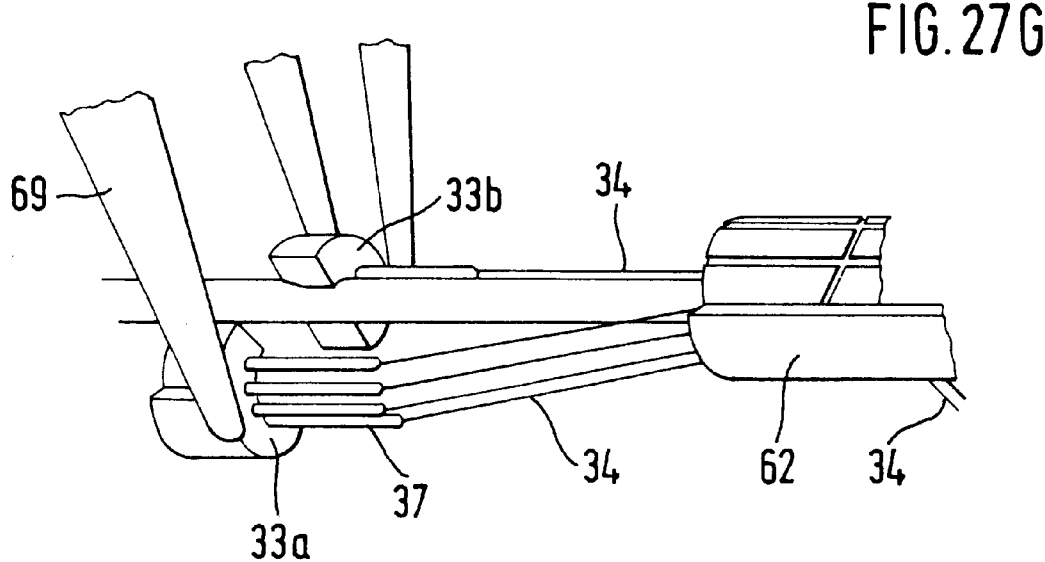
FIG. 27H
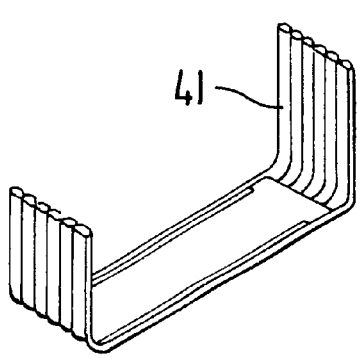
FIG. 27I
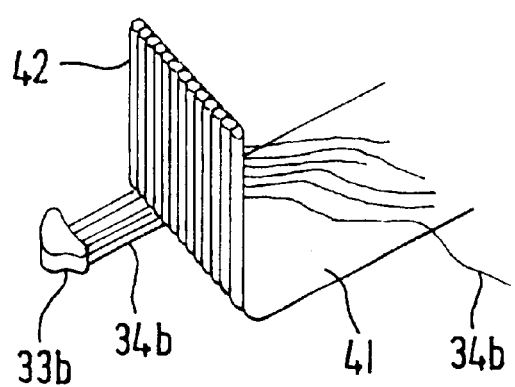

DEVICE AND PROCEDURE FOR JOINING HOLLOW ORGANS

This application is Continuation-in-Part of application Ser. No. 09/747,628, file May 25, 2001, pending.

BACKGROUND OF THE INVENTION

The present invention refers to a device and a procedure for joining hollow organs. With devices and procedures of this kind for attaching blood vessels, the suturing process, for example, can be mechanized and consequently speeded up and simplified. This is of great importance in coronary surgery, in particular for performing operations on the beating heart. Furthermore, through the use of devices and procedures of this kind a repeatable and high-quality suturing process can be carried out, so that the risk of the vessels not being leak-free is minimized or, for example, in coronary surgery that the rear wall of the blood vessel in question is also attached.

An important area of application for devices and procedures of this kind is the suturing of end-to-side anastomoses in coronary by-pass surgery, i.e. surgically applied unions of hollow organs in which one end of a vessel is sewn laterally to another one. The devices and procedures under the invention can, however, be used for sewing vessels in all other areas of vascular surgery.

Today, about 70,000 by-pass operations are performed each year in Germany alone. Anastomoses on the coronary arteries are the most difficult discipline. They require a great deal of skill and experience on the part of the surgeon, because the blood vessels here are extremely small, with an average arterial diameter of 2 mm and an average vascular diameter of 4 mm, and where the diameter of the other transplants, arteria mammaria interna, for example, is often only 2 mm. In particular, there cannot be any leakage or attachment of the rear wall of the vessel.

The manual procedure can be divided up into the following operational steps, where the attachment at the anastomosis suture represents the task which can be taken over by mechanical devices and the appropriate procedures. First of all, a thoracotomy and a sternotomy (opening and separation of the chest wall) are performed. Parallel to this, the transplant (e.g. vein) is obtained and prepared for attachment to the artery with a suitable diagonal end cut. In the next step, an incision is made into the artery as a lengthwise opening. Next the openings of the vein and the artery are joined to each other. This can be simplified and improved by means of a mechanical device. Finally, the thorax is closed up again.

Under the present art, several types of what are called staplers are currently known, which, like a paper stapler, place a clip instead of a suture. The systems are used primarily for larger vessels or for sealing off open vessels. Leaks in particular are a major problem with end-to-side staplers. Staplers of this kind are known, for example, from U.S. Pat. Nos. 5,732,872, 4,930,674 or 5,285,945.

Coupling systems, such as those described in "Review of Facilitated Approaches to Vascular Anastomosis Surgery," Werker, P. et al., The Society of Thoracic Surgeons, 1997, follow another approach to joining vessels. Coupling systems of this kind are used mostly in the intestine, or to join the blood vessels end-to-end.

A third group of procedures for connecting vessels is based on the conventional suturing technique, which has been mechanized. A system of this kind, for example, is the ArthroSew™ Suturing System from U.S. Surgical Dynamics.

The disadvantage of all these systems known from the present art is that they often do not provide any possibility for end-to-side anastomosis, or are not suitable for small vessels with a diameter of about 2 mm. In particular, they are often also not suitable for by-pass surgery.

SUMMARY OF THE INVENTION

Other applications of the present invention will become apparent to those skilled in the art when the following description of the best mode contemplated for practicing the invention is read in conjunction with the accompanying drawings.

It is, therefore, the object of the present invention to make available a procedure and a device for closing an opening in a blood vessel or for joining hollow organs, in particular for performing anastomoses, with which two hollow organs can be joined in a way that is simple, safe and of high quality, as well as being repeatable.

This task is solved by means of the device in accordance with the invention.

With the device according to the invention or the procedure according to the invention, both proximal as well as distal anastomoses can be performed in a coronary artery bypass operation (CABG), as well as anastomoses with the arteria mammaria interna as the transplant. In addition, they can be employed for closing (sewing up) a blood vessel.

The fundamental operating principle of the device under the invention and the procedure under the invention is based on simultaneously punching several needles with sutures through a vessel, where there are similar needles at the other end of the suture, which are simultaneously punched through a second vessel. By pulling the ends of the two sutures tight, placing the ends of the sutures in the cradle and tying the ends of the sutures together, the two vessels are then securely attached to each other.

This conception of the device and the procedure solves the task of joining hollow organs, specifically performing anastomoses in a simple, safe and repeatable way. The primary field of application is by-pass surgery on the heart with coronary ischemia, but in addition operations on other organs in the case of stenoses, occlusions, strictures and thromboses, for example, in peripheral arteries.

In contrast to manual attachment or the conventional procedures, there is no risk of the rear wall of the vessel being attached or the anastomosis suffering from leakage. With the device under the invention and the procedure under the invention, most operations can not only be performed on the asystolic heart, so that any additional traumatization for the patient as the result of the use of the heart-lung machine is avoided. Specifically, the attachment of very small vessels with a diameter of about 2 mm is possible in safety.

On the basis of the mechanized suturing process, the quality of the suture is improved, the rear wall is protected, for example, by means of a needle carrier designed as a shoe, and the operation can consequently be carried out in most cases on the beating heart.

Under the invention, the device for joining hollow organs has several elements, which are an elongated holder a needle carrier, which is located at one end of the holder, where the needle carrier forming a projecting overhang extends radially beyond the elongated holder, so that a plurality of needles can be disposed in a ring on this projection pointing away from the end of the holder, for example, so that they stand vertical, while their ends are connected to sutures. In this way, the needle carrier is constructed as a shoe, which protects the rear wall of the vessel from the needles when the holder is inserted into the incision in the vessel. The needles can then be splayed out at a predetermined angle and, with the assistance of a needle seat positioned on the outside of the vessel wall, pushed through the vessel wall along the circumference of the incision.

If the other side of the sutures is connected with needles in a similar carrier, the second vessel which is to be connected to the first one can be sutured in this way along the periphery of its incision, so that the two openings are joined along their circumference when the sutures are subsequently pulled tight and tied together. With this, both hollow organs are securely joined together with their openings flush and in a sealing manner.

The holder can be implemented as a table stand, for example, for the end of a transplant, if the transplant is still unattached, or as a handle for example, for the second end of the transplant or for the mammaria. In addition, the holder can be equipped with an insertion aid for the transplant, for example, the vessel undergoing anastomosis. This insertion aid can be an enlargement of the elongated holder, or be mounted in the elongated holder in such a way that after the transplant is pulled over the holder and the insertion aid, this insertion aid is expanded so that the transplant has a larger circumference. In this way the transplant can be expanded to a circumference which extends beyond the periphery of the array of needles, so that by means of axial movement in the direction of the holder, the needles can be then pushed through the vessel wall of the transplant.

Instead of being pulled over an insertion aid, the holder can also be connected to a sleeve, for example, a cylindrical hollow body. The sleeve can be furnished with a suction device. When the transplant is inserted/introduced into the sleeve, its outer wall is pulled against the inner wall of the sleeve by suction and held in position there.

In the next step the end of the transplant is cut to shape. To do this, the sleeve can have a cutting surface which is a surface not oriented parallel to the direction of its internal passage, for example perpendicular or diagonally at a predetermined angle.

Set off from this cutting surface, the sleeve has adjustable pressure pads along its circumference by means of which the transplant can be squeezed together. Then the transplant has a larger cross section in the area of the cutting surface than in the area of the pressure pads and it narrows down in the transition to the area of the pressure pads, for example, like a funnel.

If the diameter of the needle array is selected in such a way that it lies between the diameter of the two cross sections, the needles can be moved in the direction of the transplant in the axial direction of the sleeve, starting from the inside of the transplant, until they push through the wall of the transplant in the funnel-shaped area and they can be located on the outside of the transplant by a needle seat.

Since only the outside of the transplant is touching the inside of the sleeve, the endothelial layers on the inside of the transplant cannot be damaged. Consequently, both distal as well as proximal anastomoses can be performed, as well as anastomoses with the mammaria.

With respect to the artery also, it can be held by annular suction by means of a suction device before the incision is made. Kept in position like this, the incision is then made inside the suction-held area at a length matching the circumference of the transplant, and then the shoe with the needles is inserted, without the possibility that the arterial walls could collapse into the artery after performing the incision.

To protect the needles when they are being inserted, or rather to protect the vessel from the needles, a needle cap can be pulled over the needles and the needle tips, which is removed from the needles immediately before the needles are deployed, or before the needles are pushed through the vessel wall. In this way, the vessel is protected for as long as possible from the sharp-pointed needles and injuries resulting from them.

The needles can be extended in the direction of the lateral vessel wall immediately before being pushed through the vessel wall, while a sleeve is inserted between the needles and the elongated holder and the needles are splayed outwards.

All the movements of the needle cap or the sleeve, for example, or the two-part seat for pushing the needles through the vessel wall, can be carried out by simply pressing buttons, for example by using a handle which is attached to the holder and has the appropriate controls with mechanical means of movement.

Once the two openings of the vessels are sutured and the sutures drawn tight, the needle seats with the needles and the sutures attached to them can be placed in a cradle, where as the result of proper design of the cradle and proper placement of the needle seats, the sutures coming from the transplant or from the artery are correctly sorted out automatically. The matching ends of the sutures can then be tied together correctly.

Tying the sutures together can be done, for example, by means of an auxiliary instrument which takes up the parallel sutures in the cradle from the two sides (artery, transplant) and encloses them with clips. The auxiliary instrument can be designed in such a way that several clips can be placed simultaneously, or only one clip is placed at a time. If several clips are placed simultaneously, it is advantageous if the end effector of the auxiliary instrument is designed in such a way that the distance between the clips on the auxiliary instrument is equal to the distance between the sutures in the cradle.

As an alternative to the auxiliary instrument, conventional knots can continue to be made or other procedures such as bonding, thermal forming, etc. can continue to be used. In addition, clips made of nitinol, such as those produced by the Coalescent Surgical Co. Inc., can be used to join the sutures coming from the two hollow organs.

In addition to straight needles, curved needles are also conceivable.

For sewing on a arteria mammaria interna (an artery which is already on the heart and is only being sutured unilaterally), it is conceivable to design the instrument as a minimally invasive surgical instrument and to introduce it into the body through small incisions and to suture without opening the sternum. To do this, the part of the instrument for the artery and the transplant side would be introduced into the body by means of a trocar and handled endoscopically.

The handles of the tool can also be designed in such a way that they can be manipulated by a robot. In the first step, the procedure for the transplant could continue to be performed by hand and only the procedure for the artery be carried out by the robot. To do this, a flange, which is attached to a robot flange, would be installed for the artery side instead of the hand grip. The movement of the needle cap, the sleeve and the two-part seat are then controlled electrically, hydraulically or pneumatically or by other drives.

The transplant portion can also be handled by a second robot arm for the suturing of the arteria mammaria interna.

The handle with the needle carrier and the insertion aid would be flanged to a robot. The two-part seat would need to be pushed up manually or by yet another robot arm and pulled out along with the needles. The needle seat (two-part seat) is then put into the cradle by the robot, and the tightening and tying together is done manually.

Other applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein:

In what follows some examples are given of devices and procedures under the invention.

FIGS. 1a–c show an anastomosis being performed;

FIGS. 2a–c show a device under the invention;

FIG. 16 shows the set according to FIG. 15 with the needle seats removed;]

FIGS. 24a–c show an additional set in accordance with the invention;

DETAILED DESCRIPTION OF THE PREFERRED EMBODIMENT

Figure 3:
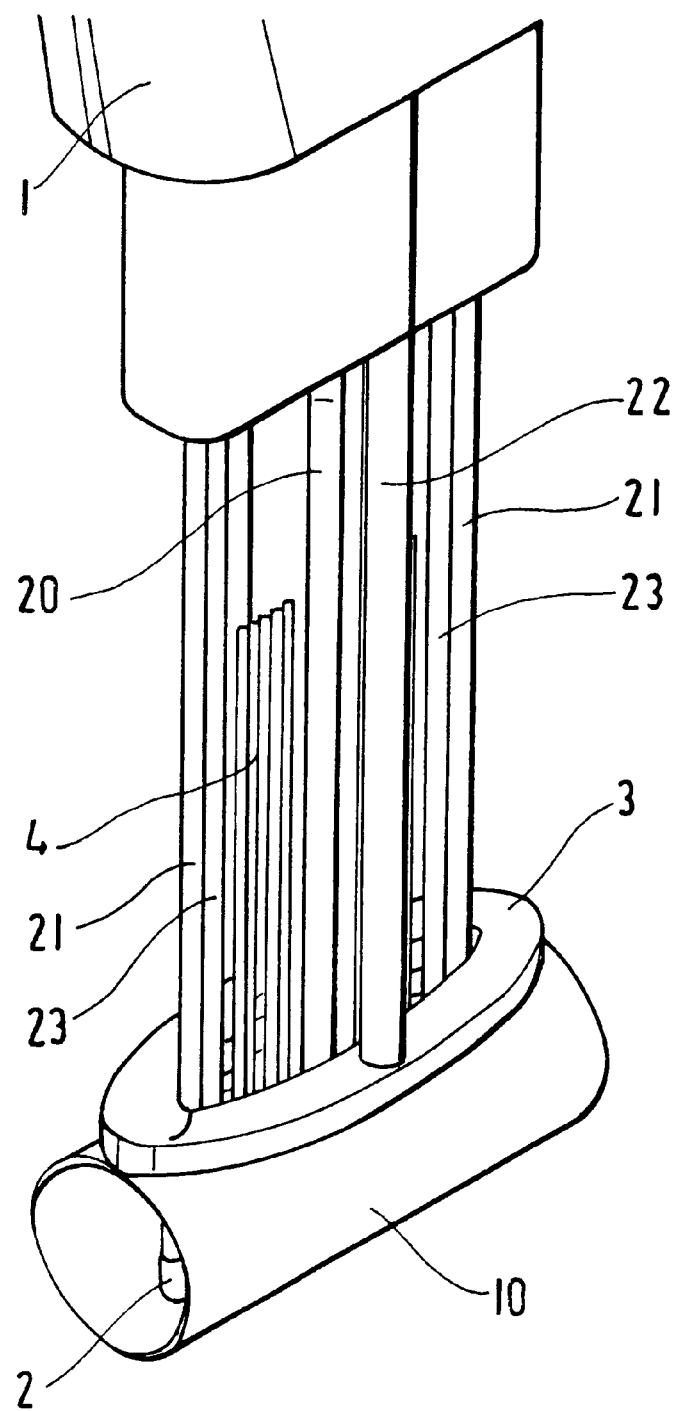
FIG. 3 shows an artery with a needle carrier inserted.

FIG. 1 shows schematically the attachment of end-to-end anastomoses. FIG. 1A shows an artery 10 and a vein 11. The vein 11 is a transplant which is to be joined to the artery 10. Here, as in all the following illustrations, similar components are identified with similar reference numbers. In FIG. 1B an incision 12 has been made in the artery 10. The end of the vein 11 has been cut on the diagonal so that a suitable opening 13 results, whose diameter approximately matches the diameter of the opening 12. FIG. 1C shows how the two openings 12 and 13 of artery 10 and vein 11 are joined to each other and sutured, so that now an end-to-end anastomosis has been performed.

FIG. 2 shows a device under the invention, which can be used when creating anastomoses shown in FIG. 1. This device has a handle 1, at the end of which a shoe 2 is formed as a needle carrier for needles. This shoe 2, along with the needles disposed vertically on it, is covered by a needle cap 9. Above the needle cap 9 there is a needle seat 3, whose function will be explained later. In addition, sections of sutures 4 are shown, which are connected to the ends of the needles.

FIG. 2B shows the lower part of the device from FIG. 2C in an enlarged view in a lateral cross section. Again, the shoe 2 can be seen, on which needles 7 are standing vertically in a ring around a holder 20. These needles 7 are connected to sutures 4 by the ends facing the shoe 2. Above the points of the needles there is a sleeve 8, which can be moved along the holder 20 by means of a sleeve linkage 23. The entire arrangement of needles 7 and sleeve 8 is covered by a needle cap 9, which can similarly be moved along the holder 20 by means of a linkage 21, and in its lowered position provides a protective covering for the needles 7 and the sleeve 8. Above this protective cover 9 there is needle seat 3, which can similarly be moved along the holder 20 by a suitable mechanism which is not shown here.

FIG. 2A now shows in a cross section rotated by 90° to FIG. 2B a needle carrier 2, which is inserted into an artery 10. The needle carrier or shoe 2 was inserted into the artery 10 through a suitable incision not shown in the cross section and then, as shown in FIG. 2A, the needle cap 9 was raised. As a result, the needle points are now exposed inside the artery, but the rear wall of the artery is protected from the needles 7 by the shoe 2.

Both the sleeve 8 and the needle cap 9 can be moved up or down by means of their corresponding linkages 23 or 21 through push buttons 5 or 6 on the handle 1, as shown in FIG. 2C.

FIG. 3 shows the same arrangement as in FIG. 2B, however in an external view of the artery 10. It can be seen clearly here that the needle seat 3 can be separated into two, where the needle seat 3 can be moved along the holder rod 20 by means of the linkage 22.

Figure 4:
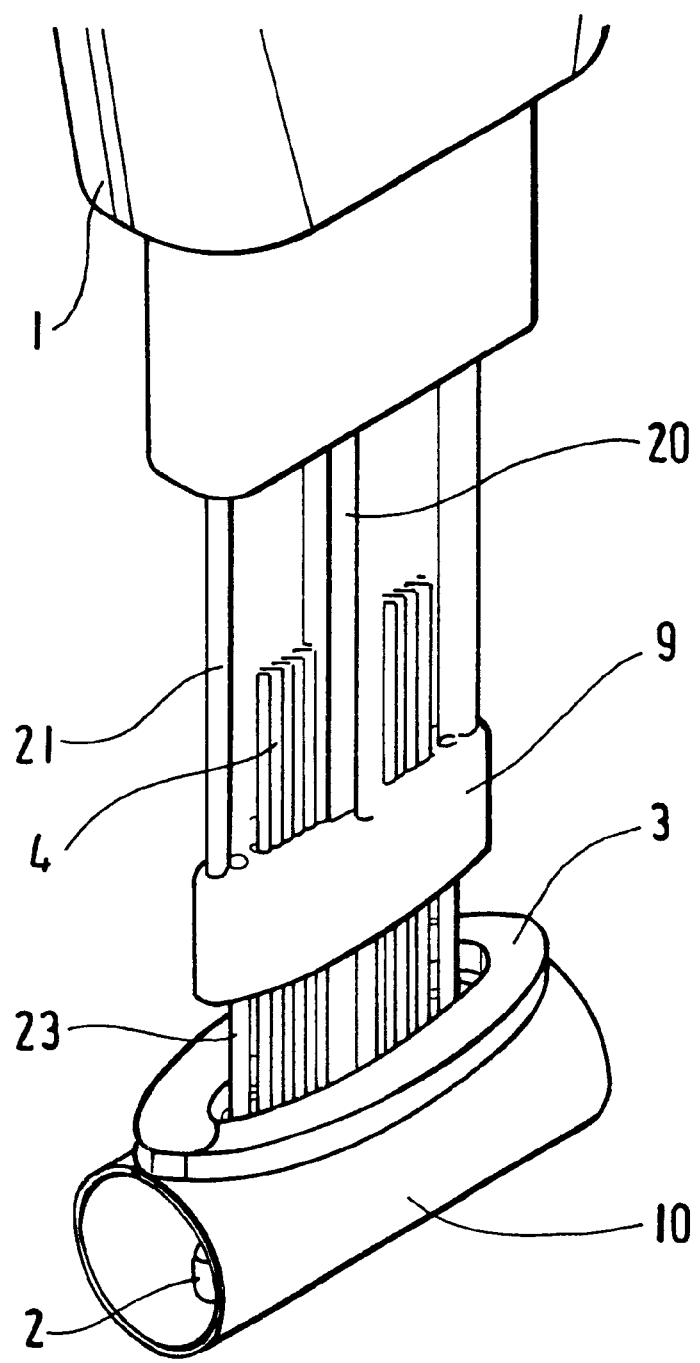
FIG. 4 shows a needle carrier inserted with needle cap raised.

FIG. 4 shows a similar view as in FIG. 3, where however the position of the individual parts corresponds to that in FIG. 2A, i.e. the needle cap 9 has been pulled off the shoe 2 out of the opening in the artery 10 by means of its linkage 21.

Figure 5:
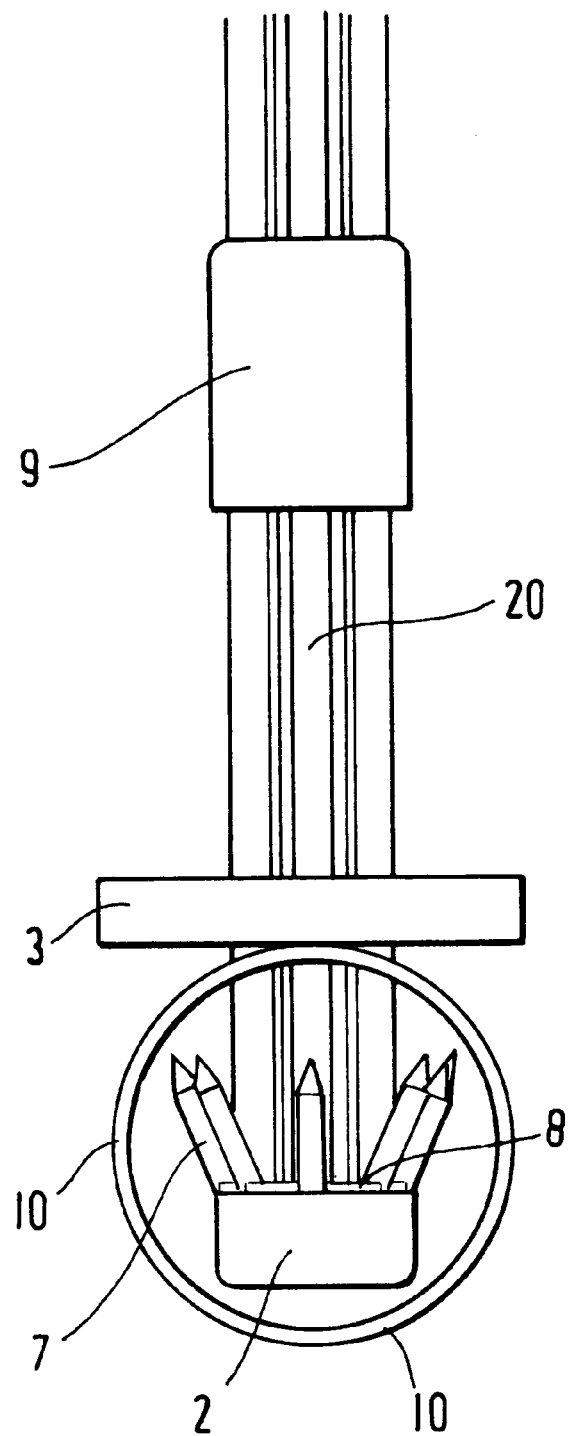
FIG. 5 shows the arrangement according to FIG. 4 in cross section.
Figure 6:
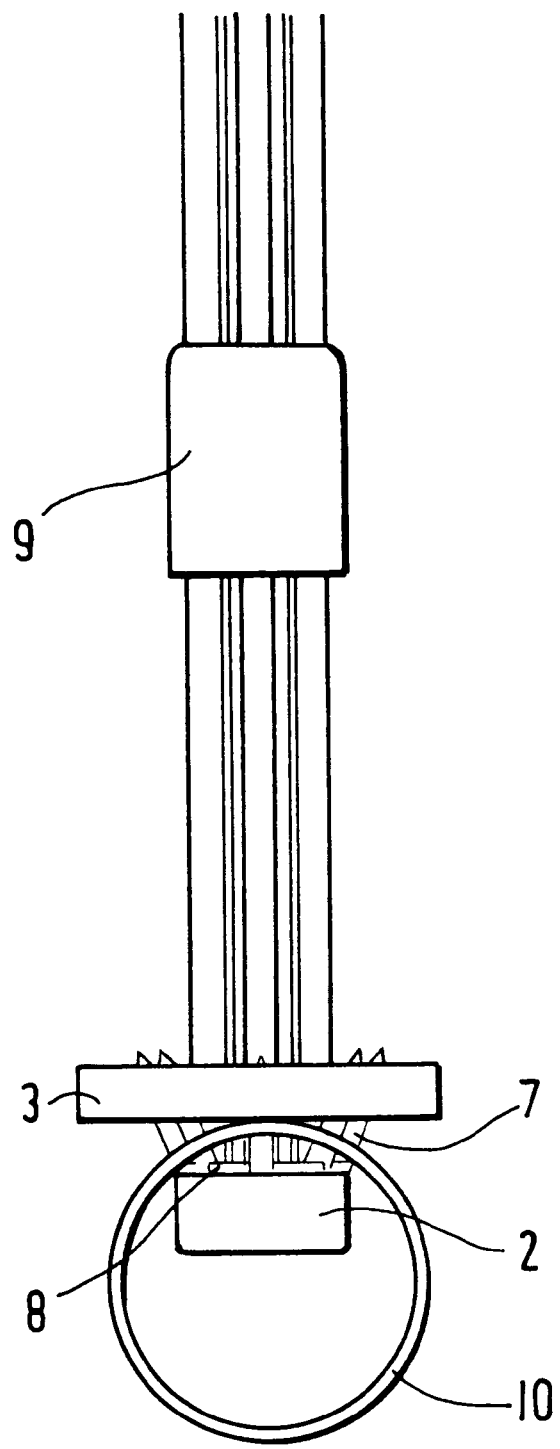
FIG. 6 shows a cross section through an artery with a needle carrier inserted, penetrating the vessel wall.

FIG. 5 shows the next step during the performance of the anastomosis, where the sleeve 8 has been pushed between the needles and the holder linkage 20 by means of its linkage, so that the needles are now standing sideways at an angle and are spread out radially. If the shoe 2 is now pulled up, or the needle seat 3 is pushed down, the tips of the needles 7 are pressed through the wall of the artery 10 along the circumference of the incision and they come to a stop in the needle seat 3. This is shown in FIG. 6, where following this position, the needle seat 3 can be withdrawn upward or opened, and the two halves of the needle seat 3a and 3b can be withdrawn laterally.

Figure 7:
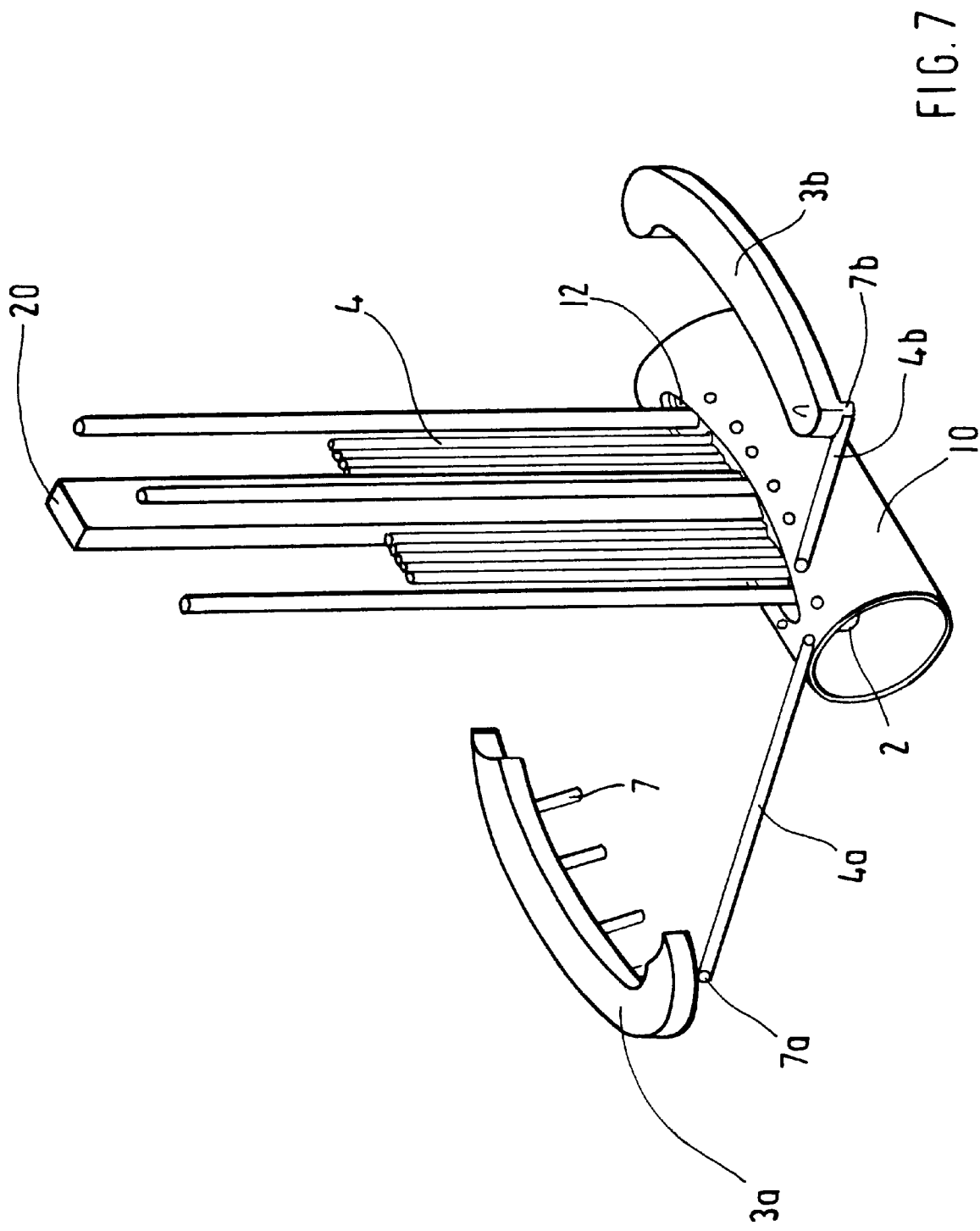
FIG. 7 shows an artery with a vessel wall sutured.

This is shown in FIG. 7, where it is can be seen that the needles are being removed together with the halves of the needle seat 3a and 3b, where they are pulling the sutures, here 4a and 4b, which are attached to them, through the suture holes.

Not all the sutures which come from the ends of the needles are shown in FIG. 7 for the sake of clarity. But it must be made quite clear at this point that the end of each needle is provided with its own suture, which runs through the corresponding suture opening into the interior of the artery and then along the holder 20 and out of the incision.

With this step, the first half of performing an anastomosis is concluded. Next comes the suturing of the opening of the vessel to be attached, for example, of a vein.

Figure 8:
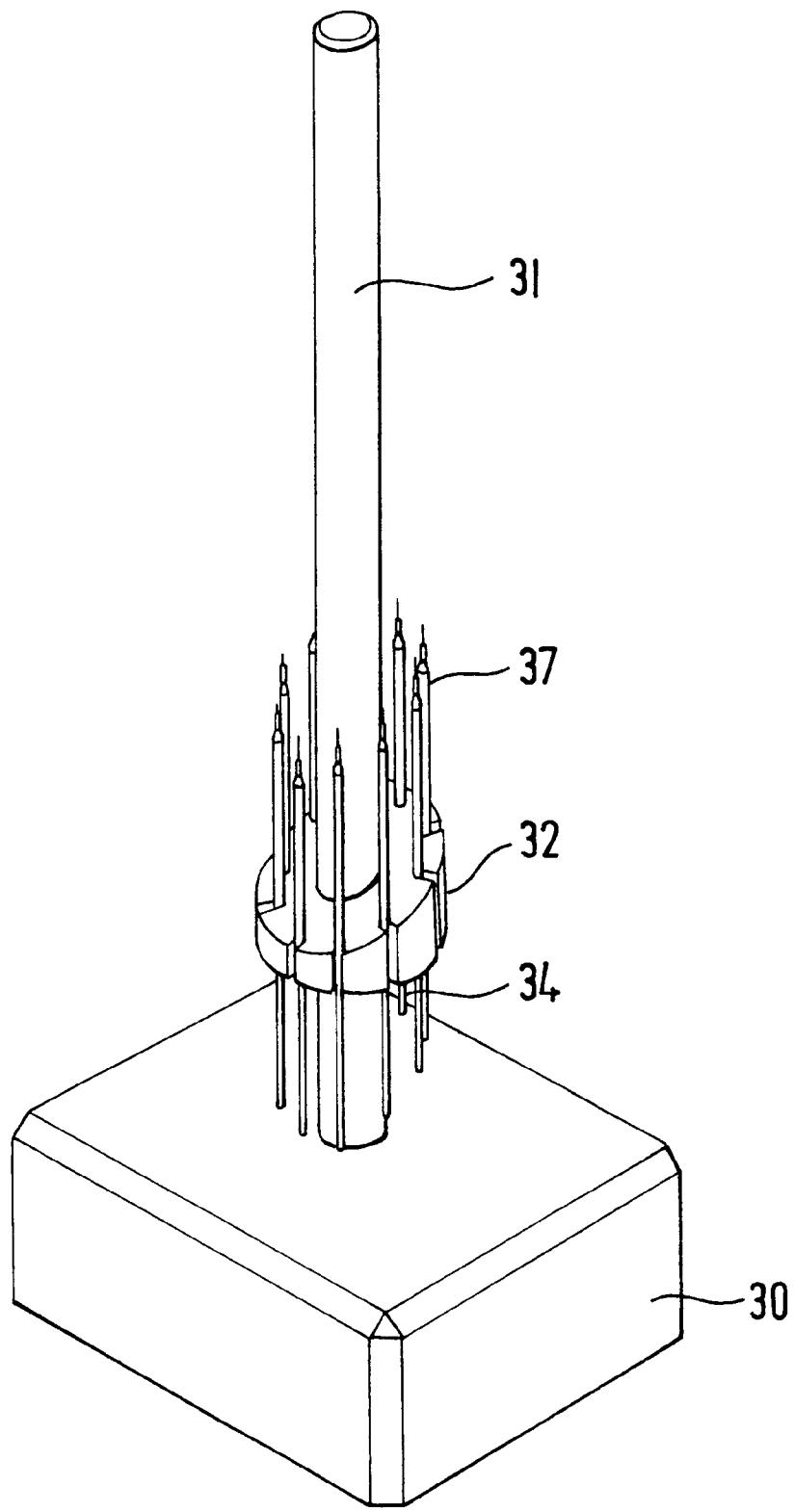
FIG. 8 shows another device under the invention.

FIG. 8 shows a suitable device, where, instead of a handle, a table stand 30 is being used, which has a center rod 31 as well as a needle carrier 32, in which needles 37 are disposed in a circle around the center rod 31. These needles 37 are connected at their ends to sutures 34. It should be noticed that matching the diagonal cut at the opening of the vein, as shown in FIG. 1, the needle carrier is beveled in the same way.

Figure 9:
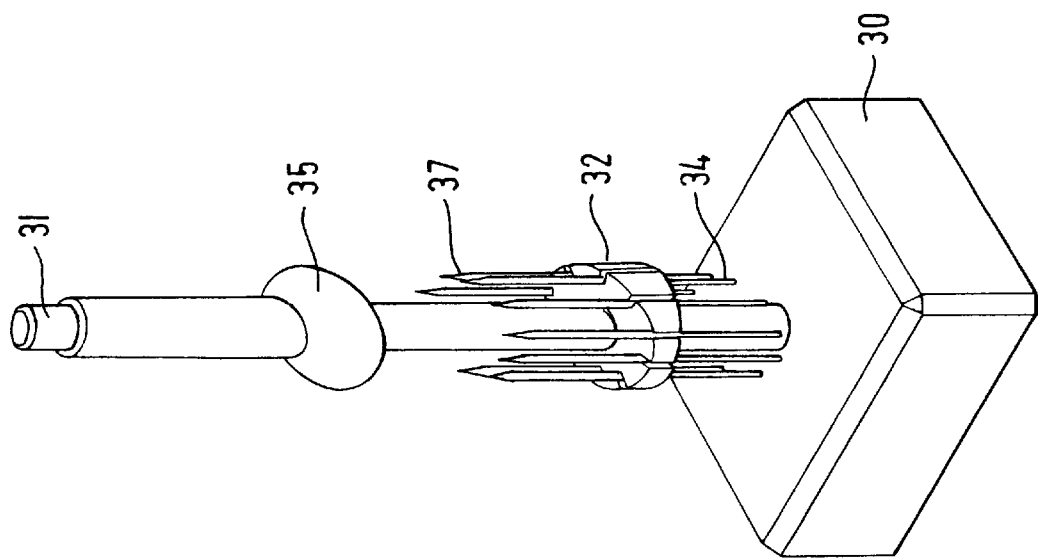
FIG. 9 shows the device from FIG. 8 with the vessel expanded.

FIG. 9 shows the device from FIG. 8, where an installation aid or insertion aid 35, which is enlarged in one section, is mounted over the central rod 31. Alternatively, the insertion aid can be designed just to be dilatable, for example, by suitable inflation.

Figure 10:
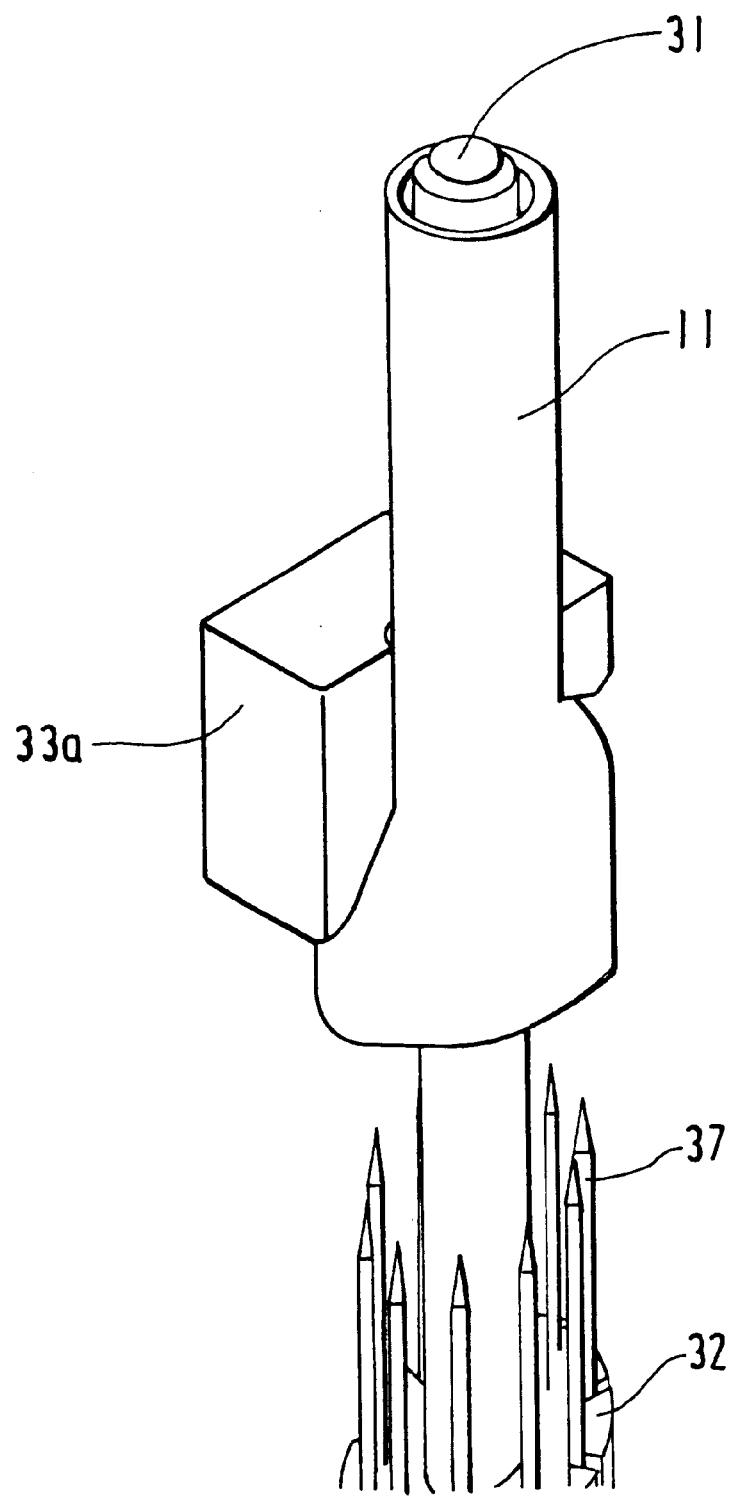
FIG. 10 shows the device according to FIG. 9 with the vein pulled down over it.

FIG. 10 shows another section from a device in accordance with FIGS. 8 and 9, where a vein 11 is now pulled over the insertion aid 35. The vein is now similarly greatly stretched in the enlarged section of the insertion aid, where the diameter of the vein in the stretched area is greater than the diameter of the needle arrangement with the needles 37. In FIG. 10 it can also be seen that one half 33a of a two-part needle seat is placed on the vein above the enlarged area.

Figure 11:
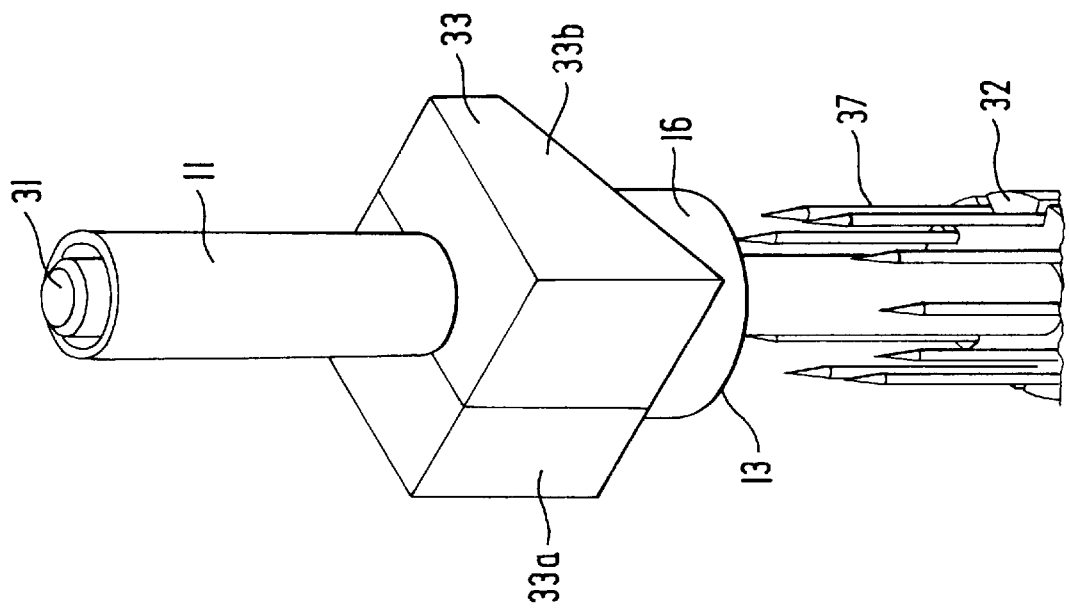
FIG. 11 shows the device according to FIG. 10 with the needle seat.

In FIG. 11 the needle seat 33 has been fully assembled from its two halves 33a and 33b.

Figure 12:
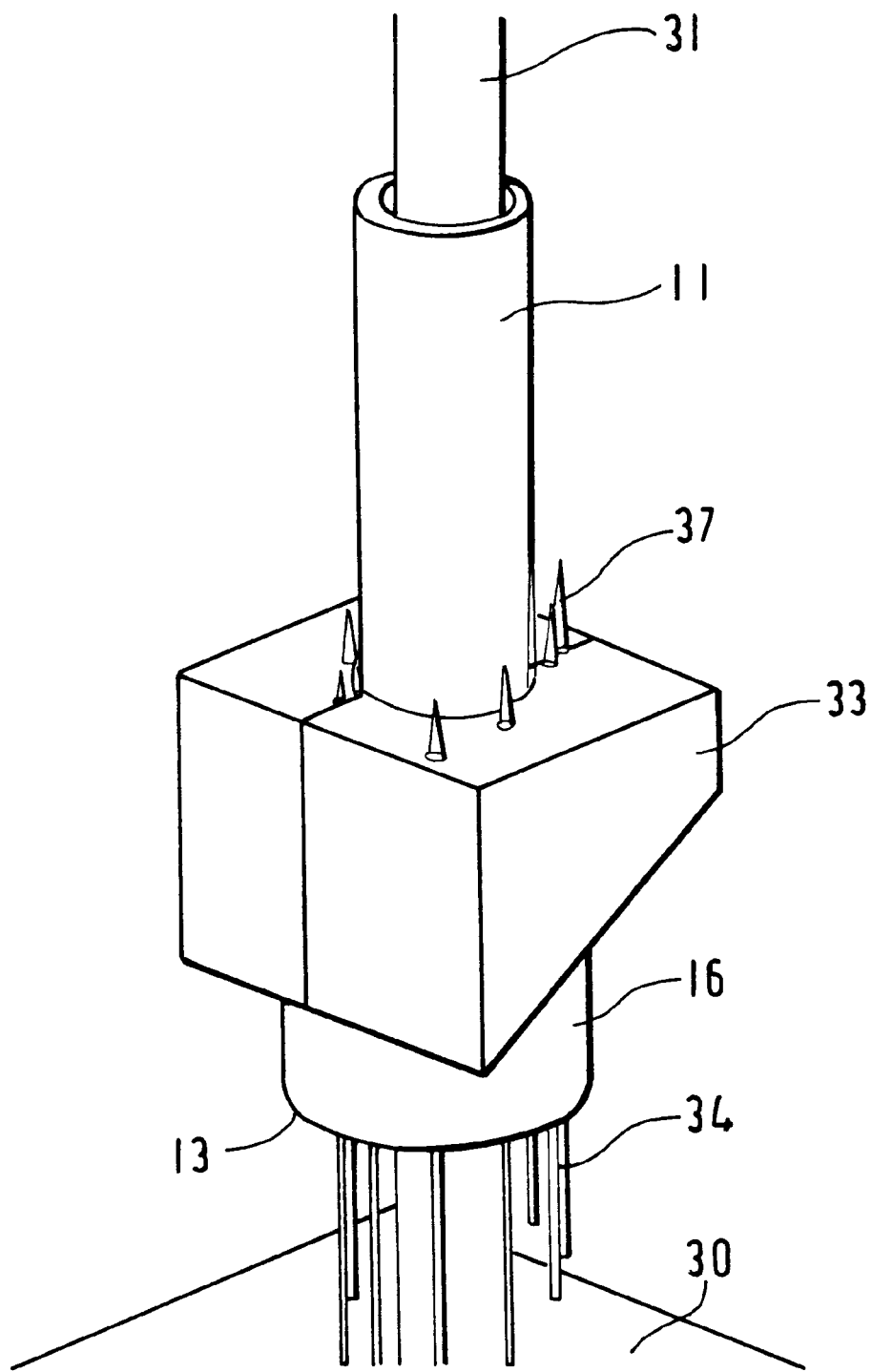
FIG. 12 shows the device according to FIG. 11 with a sutured vessel wall.

In FIG. 12 it can be seen that the needles are now being pushed axially along the center rod 31, or the vein with the seat 33 is being pushed in the direction of the needles, so that the needle points pierce the vein wall from inside the vein and come to a stop in the seat 33.

Figure 13:
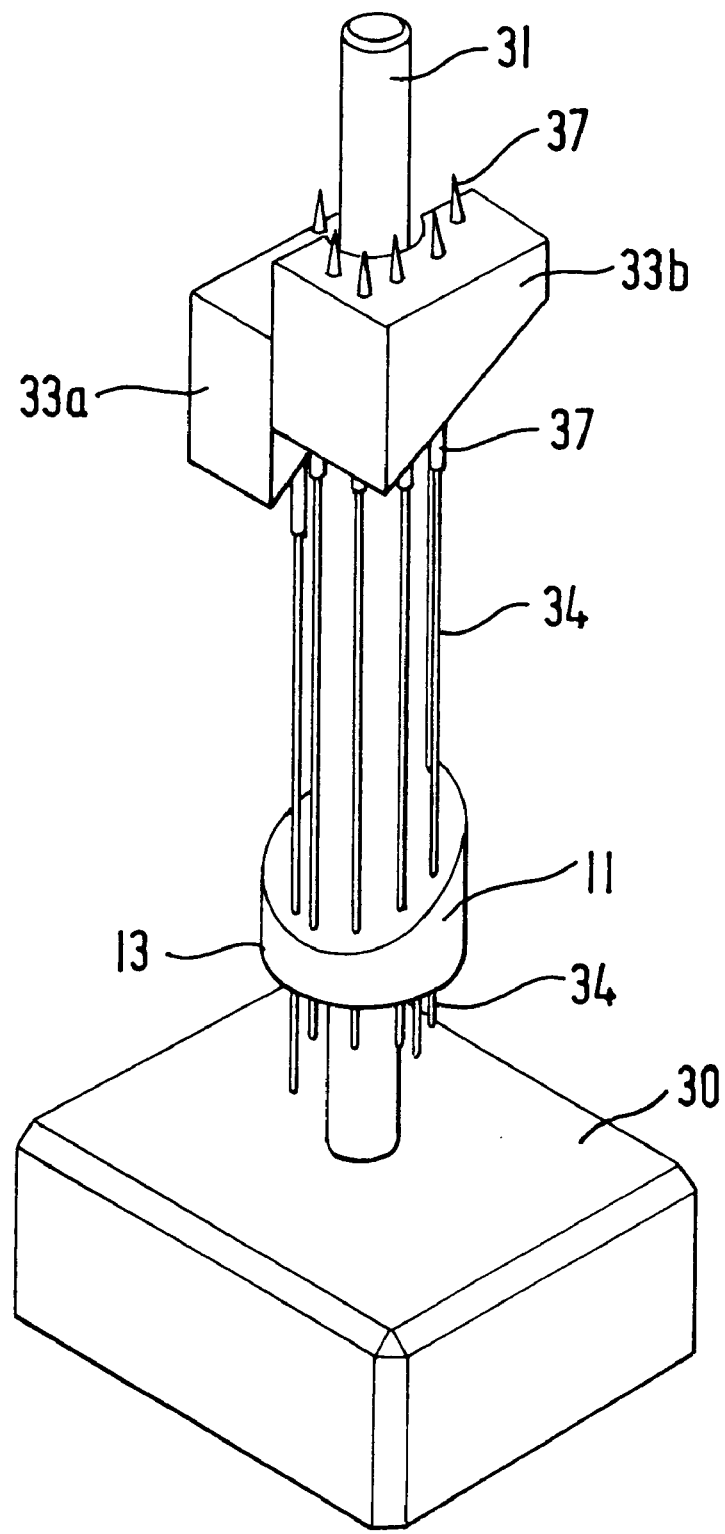
FIG. 13 shows the device according to FIG. 12 with the needle seat removed.

FIG. 13 shows how the two parts of the needle seat 33a and 33b are pulled away upwards from the expanded part of the vein, whereby the sutures 34, which are attached to the ends of the needles 37, are pulled through the corresponding suture holes in the vein 11. This pulls the corresponding sutures through the opening 13 of the vein, so that the two openings 12 or 13 of artery 10 or vein 11 respectively can now be joined to each other.

For this, FIGS. 14A and 14B once more show a holder corresponding to FIG. 2 with a handle 1, and in FIG. 14B the overall arrangement of shoe 2 with needles and sutures 4 and the table stand 30 with needles 37 and sutures 34. As can be seen, the open ends of the sutures in both arrangements are attached to each other in each case. After the wall of both the artery and the vein have been pierced, the sutures 4 or 34 consequently run from outside the vein through a suture hole in the vein into the interior of the vein, from there into the interior of the artery and out again through a hole pierced in the wall of the artery.

FIG. 14C, and in a section from it FIG. 14D, show an alternative to the table stand 30. Here the needle holder 32 with the needles 37 is attached to a handle 40, where the handle ends in a tip over which the vein can be pulled in a suitable way. Installation aids or insertion aids, as described above, can be attached here.

Figure 14:
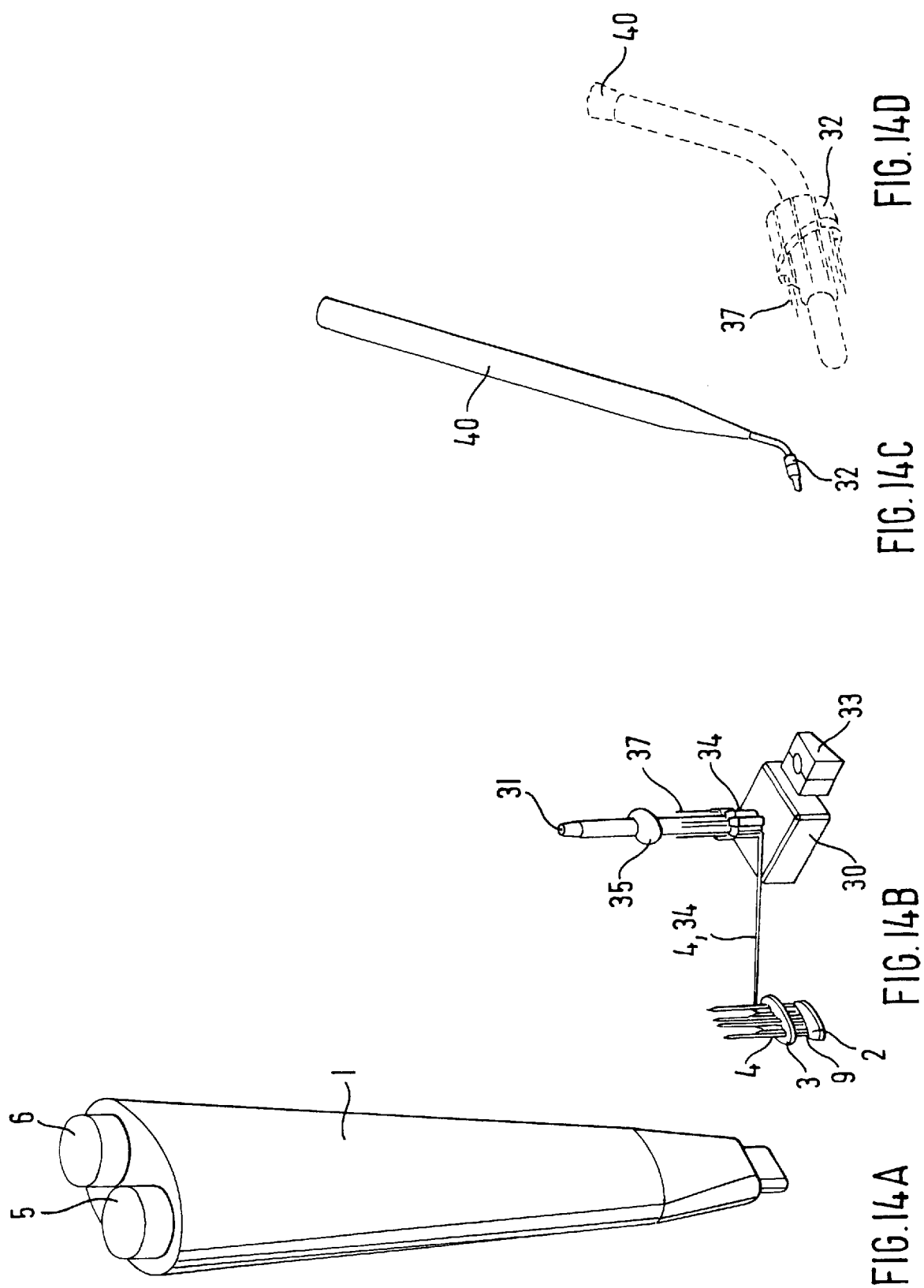
FIGS. 14a–d show a set under the invention.
Figure 15:
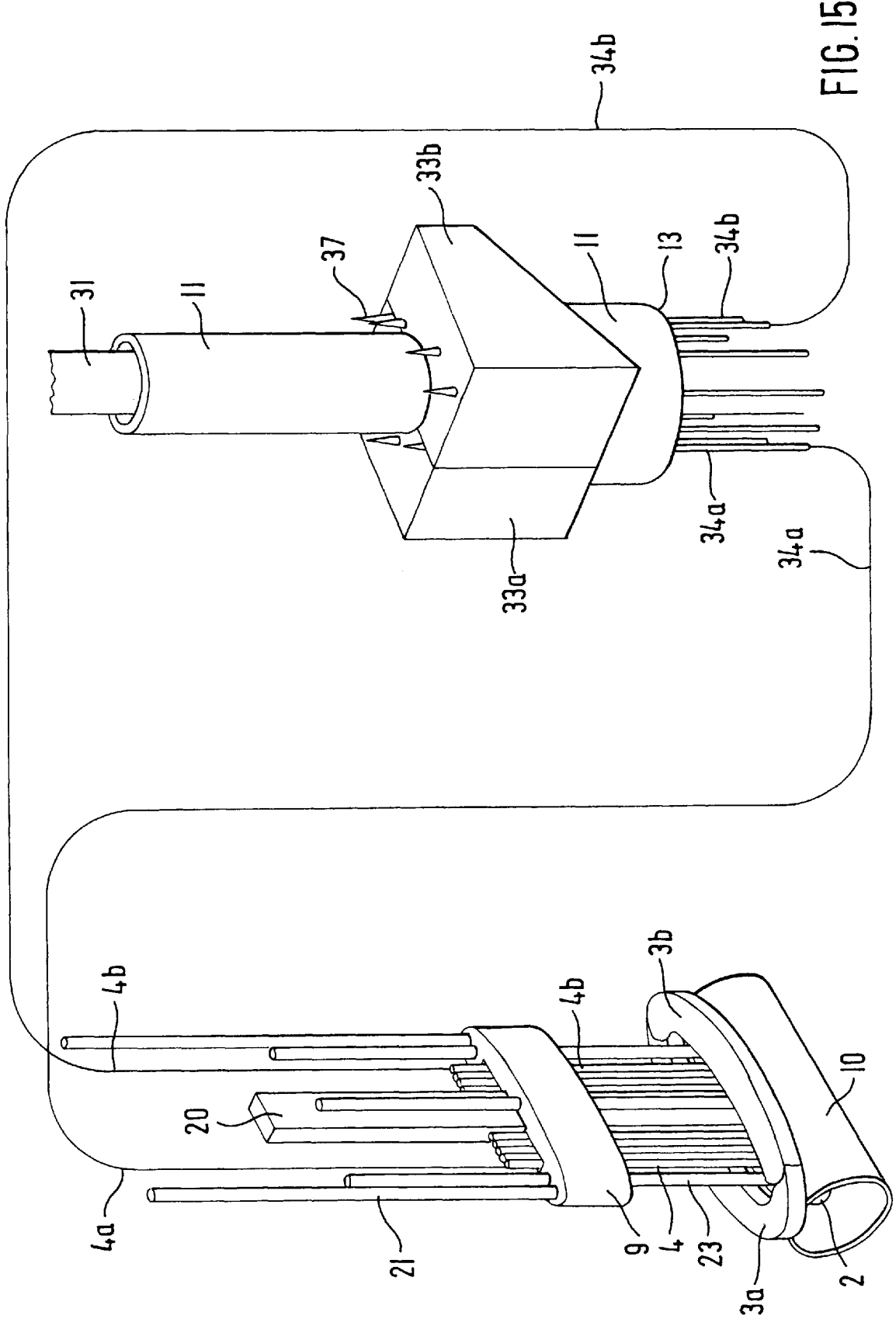
FIG. 15 shows the schematic of a set under the invention during suturing of a vessel.

FIG. 15 shows the drawing in FIG. 14B in enlarged form. The sutures are shown in two examples 4a, 4b or 34a, 34b respectively. Otherwise the drawings correspond to the illustrations in FIG. 4 or 12 respectively.

FIG. 16 shows the illustration with the divided seat 3a, 3b or 33a, 33b respectively pulled back, where again only two sutures 4a, 34a or 4b, 34b respectively are shown as examples. Otherwise the illustration in FIG. 16 corresponds to the illustrations from FIG. 7 and FIG. 13.

Figure 17:
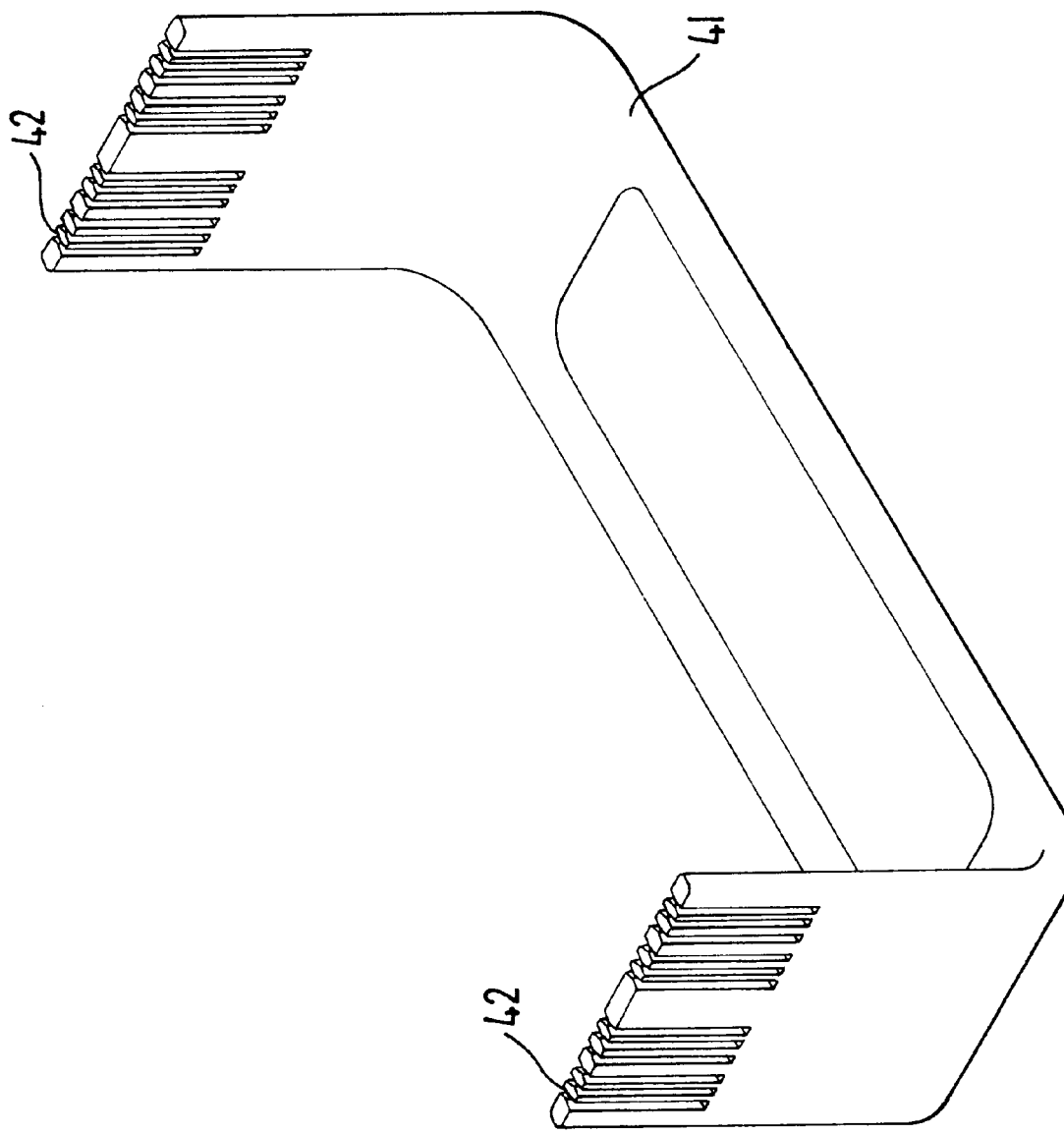
FIG. 17 shows a needle seat cradle.

FIG. 17 shows a cradle 31 for the split needle seat from FIG. 16. This cradle 41 has slit-like openings 42, the distance between which matches the distance between the sutures which come from the divided seats 3a, 3b or 33a, 33b respectively.

Figure 18:
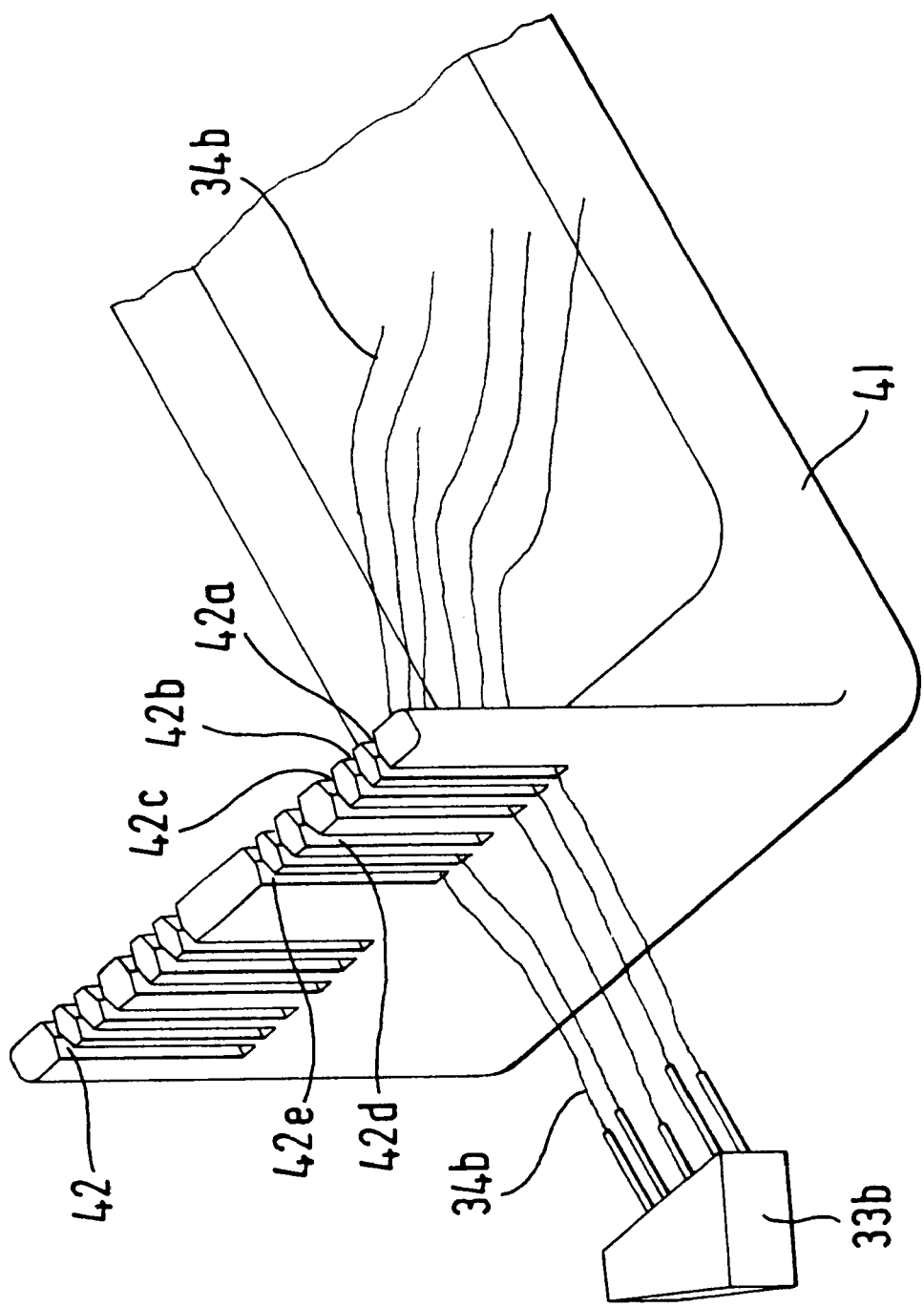
FIG. 18 shows a section of the needle seat cradle from FIG. 17 with the needle seat in place.

FIG. 18 shows how one seat 33b is placed into the cradle 41.

The slit-like openings 42 here are designated by the reference numbers 42a through 42e, where only suture 34b which is running through slit 42e, is given a reference number.

Figure 19:
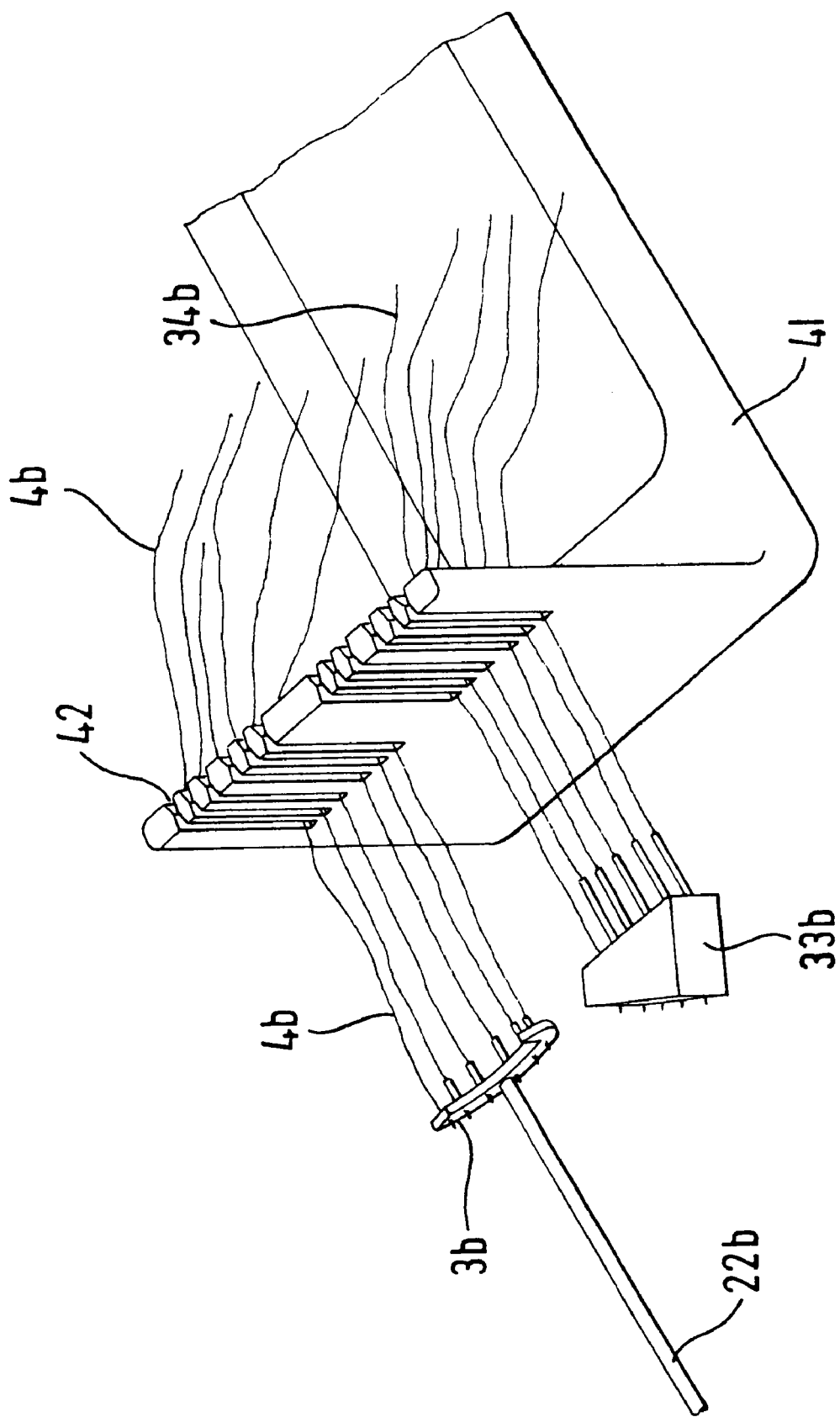
FIG. 19 shows the cradle according to FIG. 18 with two needle seats in place.

FIG. 19 shows how one half 3b of a needle seat and one half 33b of an additional needle seat are placed next to each other in the cradle 41.

Figure 20:
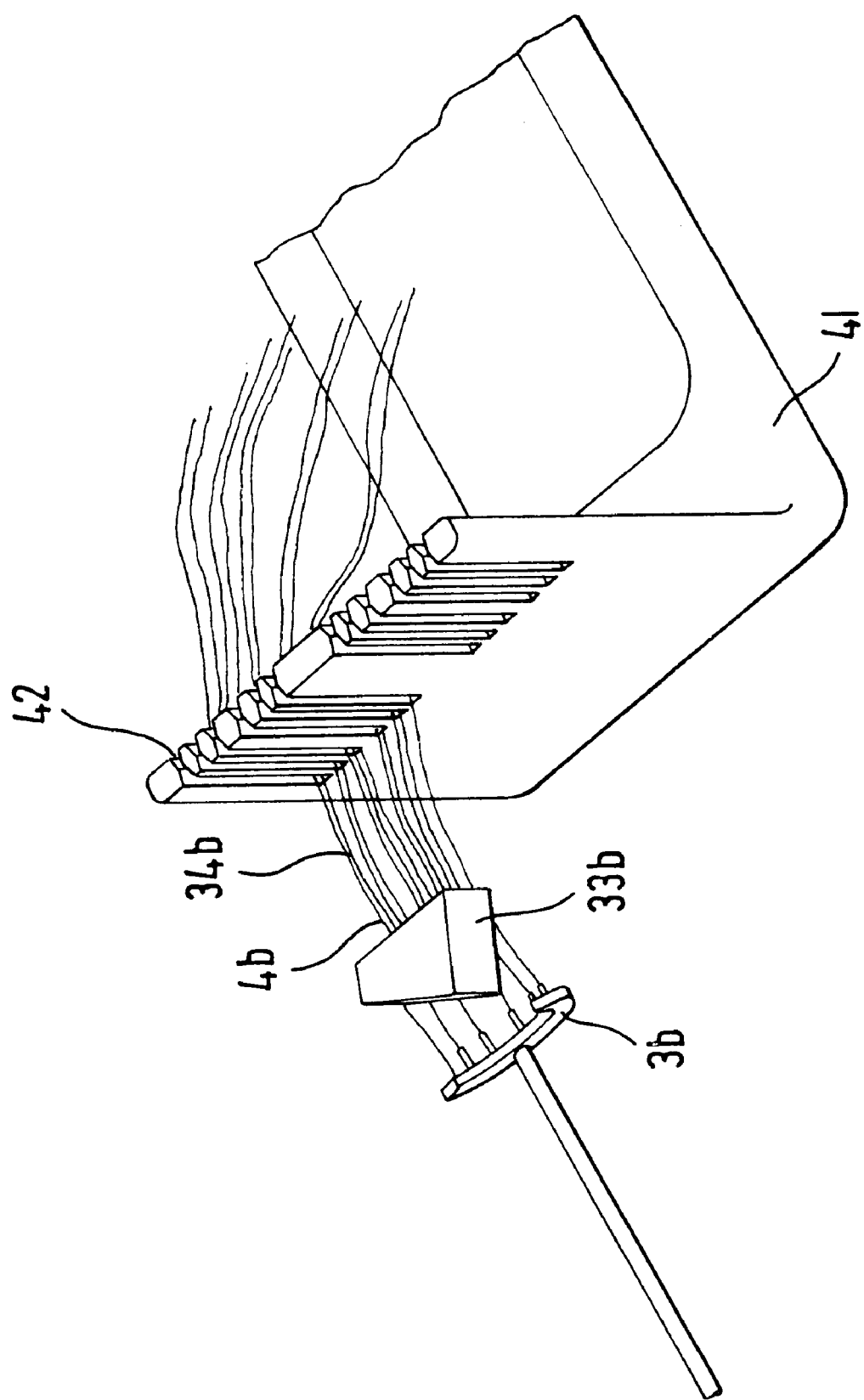
FIG. 20 shows the cradle according to FIG. 19 with needle seats placed one over the other.

In order to tie the ends of the respective sutures together correctly, the seat 33b is laid in a suitable way over the seat 3b (FIG. 20). As a result, the two ends of the same suture, shown for example as 4b and 34b, are automatically located in each of the slits 42.

Figures 21A, 21B:
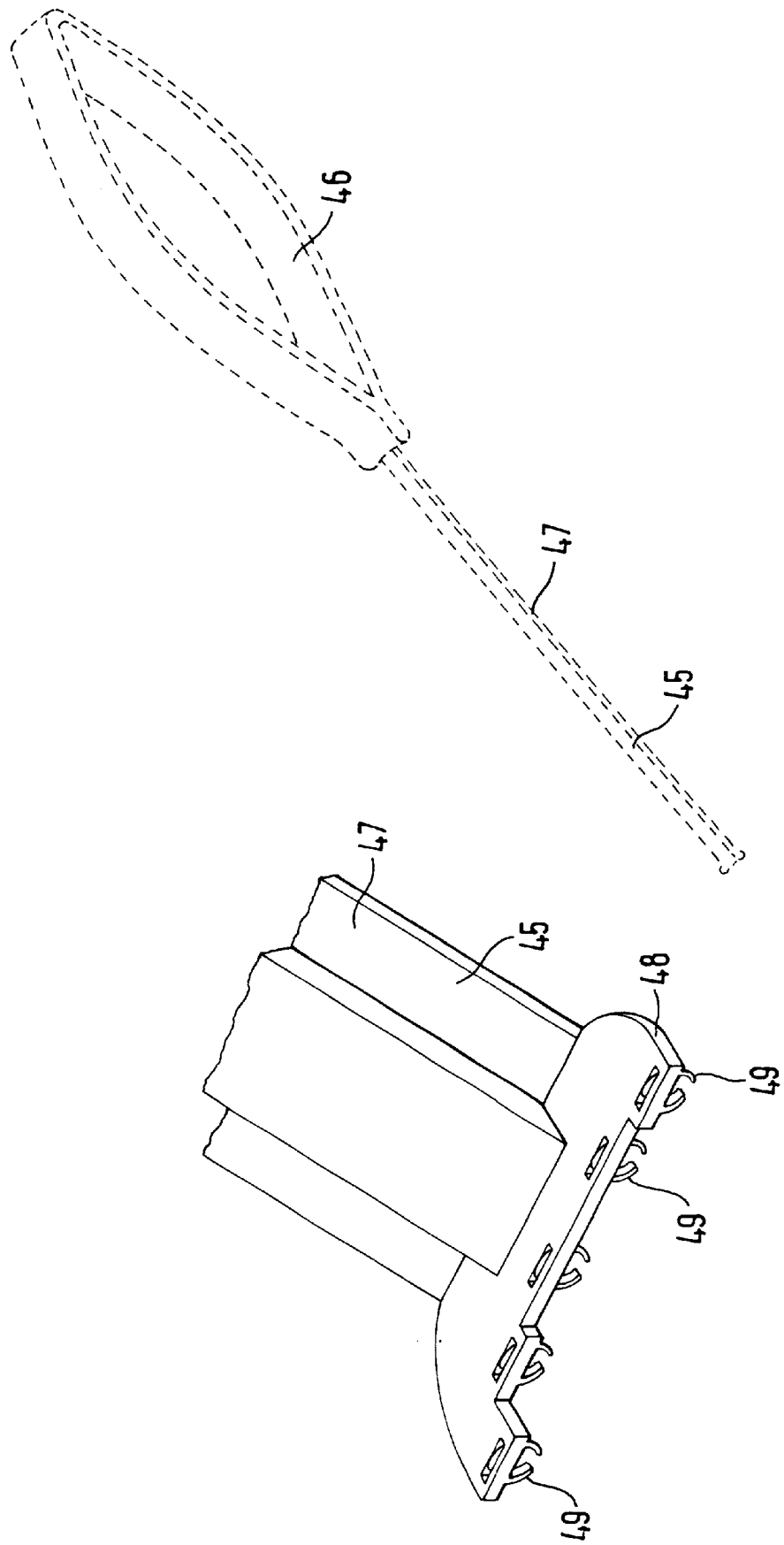
FIGS. 21a–b show a device for clipping the ends of sutures.

The ends of the sutures can be clipped together by means of a auxiliary instrument. FIG. 21 shows such an instrument, where the entire instrument 45 with grip 46 and shaft 47 is shown in FIG. 21B, while FIG. 21A brings only the end of the shaft 47. A clip holder 48, which can hold up to five clips 49 is positioned at the end of the shaft 47. With the aid of these clips 49 the specific suture ends can be attached to each other.

Figure 22:
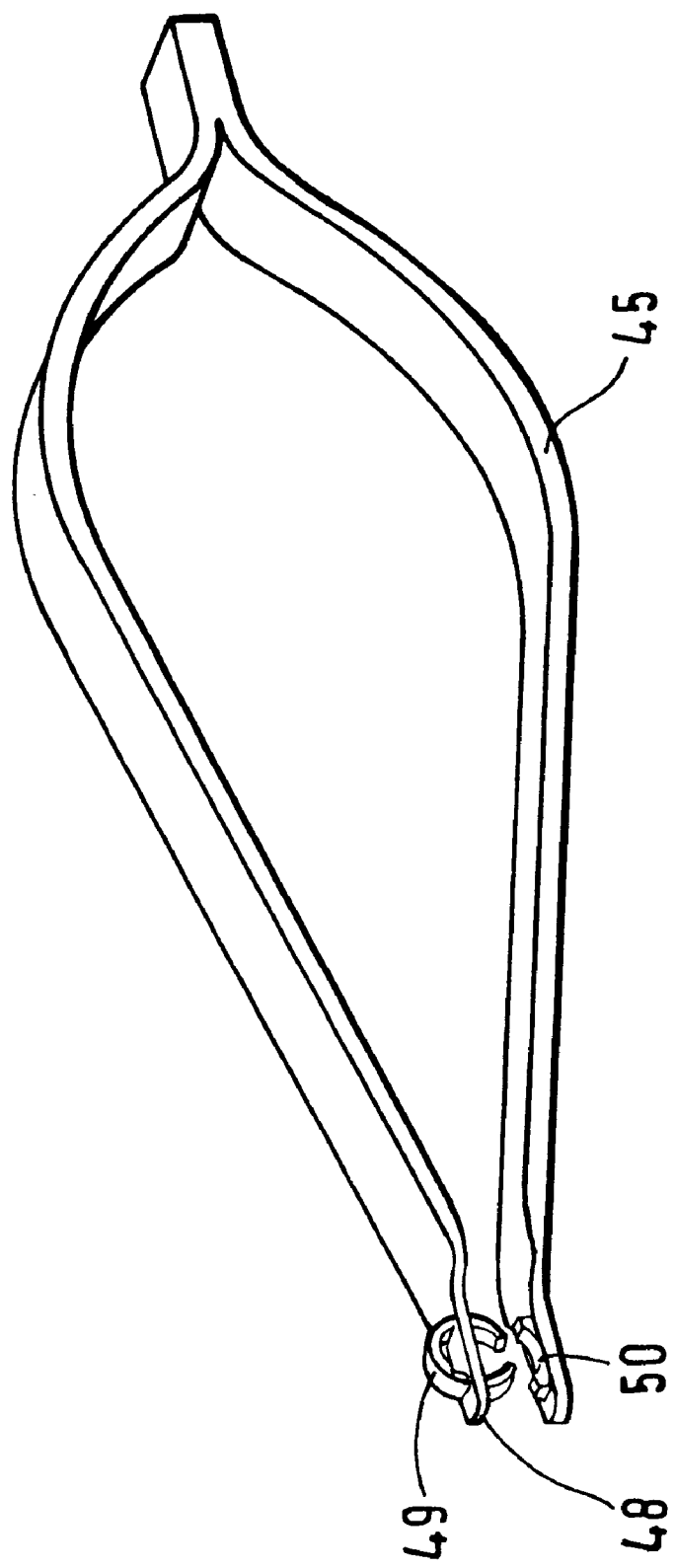
FIG. 22 shows another device for clipping sutures.

FIG. 22 shows another auxiliary instrument 45, which, however, has a clip holder for only one clip 49. Instead, the instrument 45 from FIG. 22 has a tong-like anvil 50, so that two ends of the same suture can be clipped together in a simple fashion with this instrument 45.

It must be noted in the case of the procedures under the invention that before the ends of the sutures are clipped together the sutures from the artery side and the transplant side are pulled tight, so that the opening in the vein lies completely and in a sealing manner on the incision in the artery. Then the sutures can be clipped together in this tightly approximated position.

As an alternative to an auxiliary instrument, such as the one shown in FIGS. 20 and 21, the ends of the sutures can, of course, be knotted in the conventional manner or other procedures such as adhesive bonding, thermal forming and similar methods can be employed. Clips made of nitinol (Coalescent Surgical Co., Inc.) can also be used.

Figure 23B:
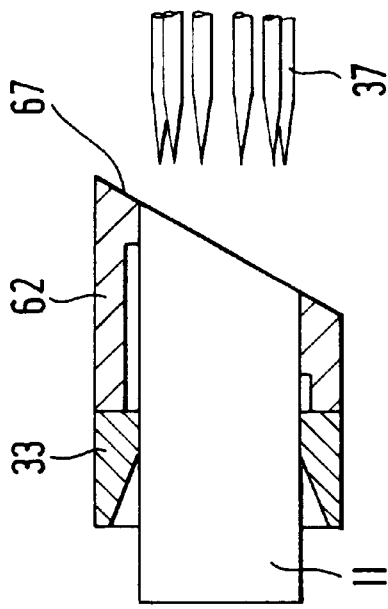
FIGS. 23a–c show an additional device in accordance with the invention.
Figure 23C:
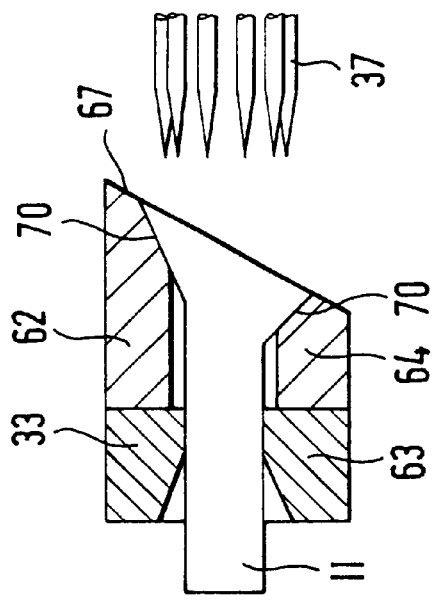
Figure 23A:
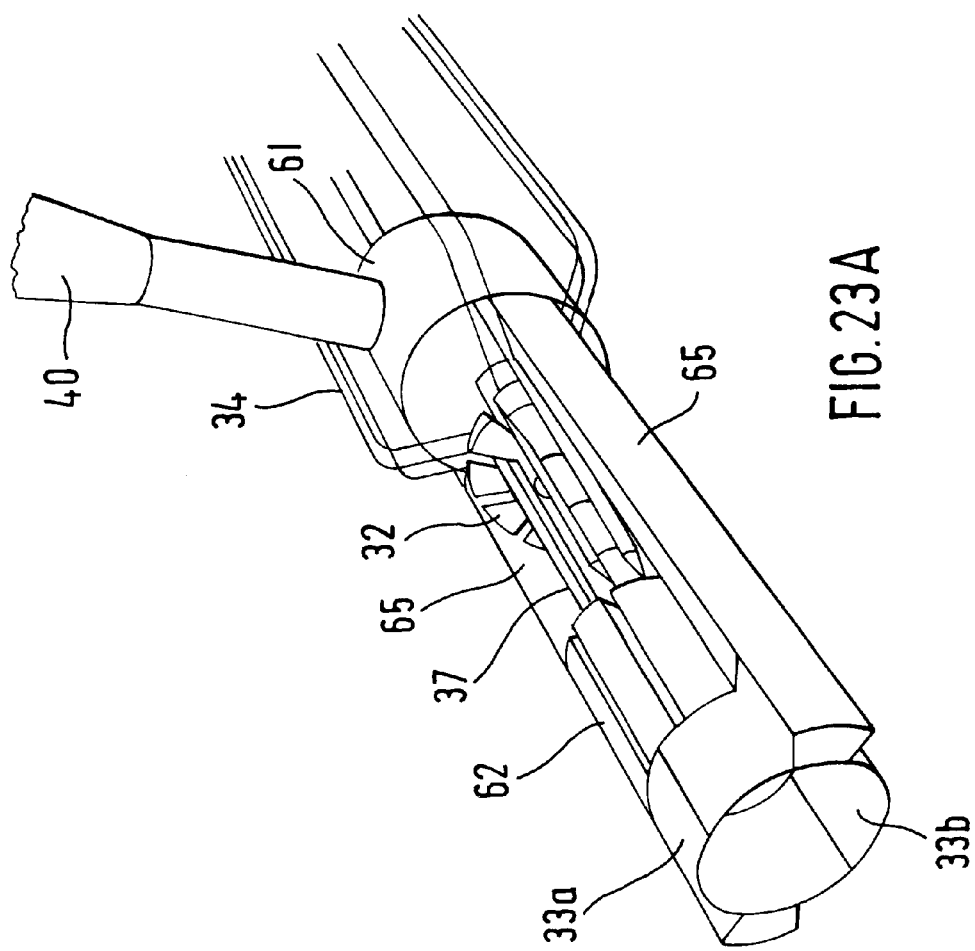

FIG. 23 shows a further embodiment for a device which corresponds to the one from FIG. 8. This device has a handle 40 to which a base 61 is attached. The base 61 acts as a holder for the needle carrier 32 in which needles 37 are disposed in an annular arrangement. A needle seat 62 is positioned in an axial direction to this annular arrangement 37, with passages which extend in the axial direction of the individual needles and through which the needles are passed during an axial movement of the needle array 37.

Another needle seat 33A and 33B is located adjacent to the seat 62, into which the needles are introduced with the axial movement. This seat 33 is a divided seat, which can be subsequently separated into two halves 33a and 33b and removed with the needles 37 sticking in them.

Both the seat 62 and the needle seat 33 are formed as hollow bodies with passages extending in the axial direction of the needle array 37.

The seat 62 and the needle seat 33 are attached to the base 61 by means of an external bar-shaped bracket 65.

As can be seen from FIGS. 23B and 23C, the seat 62 and the needle seat 33 are shaped in such a way that the cross-section of their passage can be made narrower. This can be achieved, for example, by creating air cushions. FIG. 23B shows how a transplant 11 is inserted into the passage of the seats 62 and 33. FIG. 23C shows how, by means of the pressure cushions the seats 33 and 62, the cross section of the passage and along with it the diameter of the transplant 11 is constricted locally, so that the cross section of the transplant remains unchanged only at the surface of the seat 62. The transplant narrows down consequently starting from this surface 67 in a funnel shape in the axial direction of the needles 37. The largest diameter of the passage of the seat 62 is now adjusted so that it is larger than the diameter of the ring of the needle array 37. The constriction by means of the pressure cushions in the seats 33 and 62 continues down to a diameter that is smaller than the diameter of the needle array 37. This creates a transition zone for the transplant in which the transplant tapers down in a funnel shape. If the needles are now punched through the transplant in an axial direction, they penetrate the transplant in the expanded area along the edge of the incision 67 and are pushed through the transplant in the funnel-shaped area 70.

It is advantageous if the seat 62 and/or the needle seat 33 are furnished with a device to apply a vacuum to the inner surface of their passage. In this case the transplant 11 can have suction applied on its outside and be held in position in this way. By holding the transplant in position by means of suction applied to the outside, damage to the inside of the transplant, particularly the endothelium, is avoided.

FIG. 24 shows the set up of the device for suturing the transplant and the artery.

The needles in both devices are connected to each other by means of sutures 34, where, just as in FIG. 14, only a part of the sutures is shown. For a further explanation, reference is made to the appropriate FIG. 14, where only the device shown there for suturing the transplant has been replaced by the device from FIG. 23 for suturing the transplant.

Figure 25:
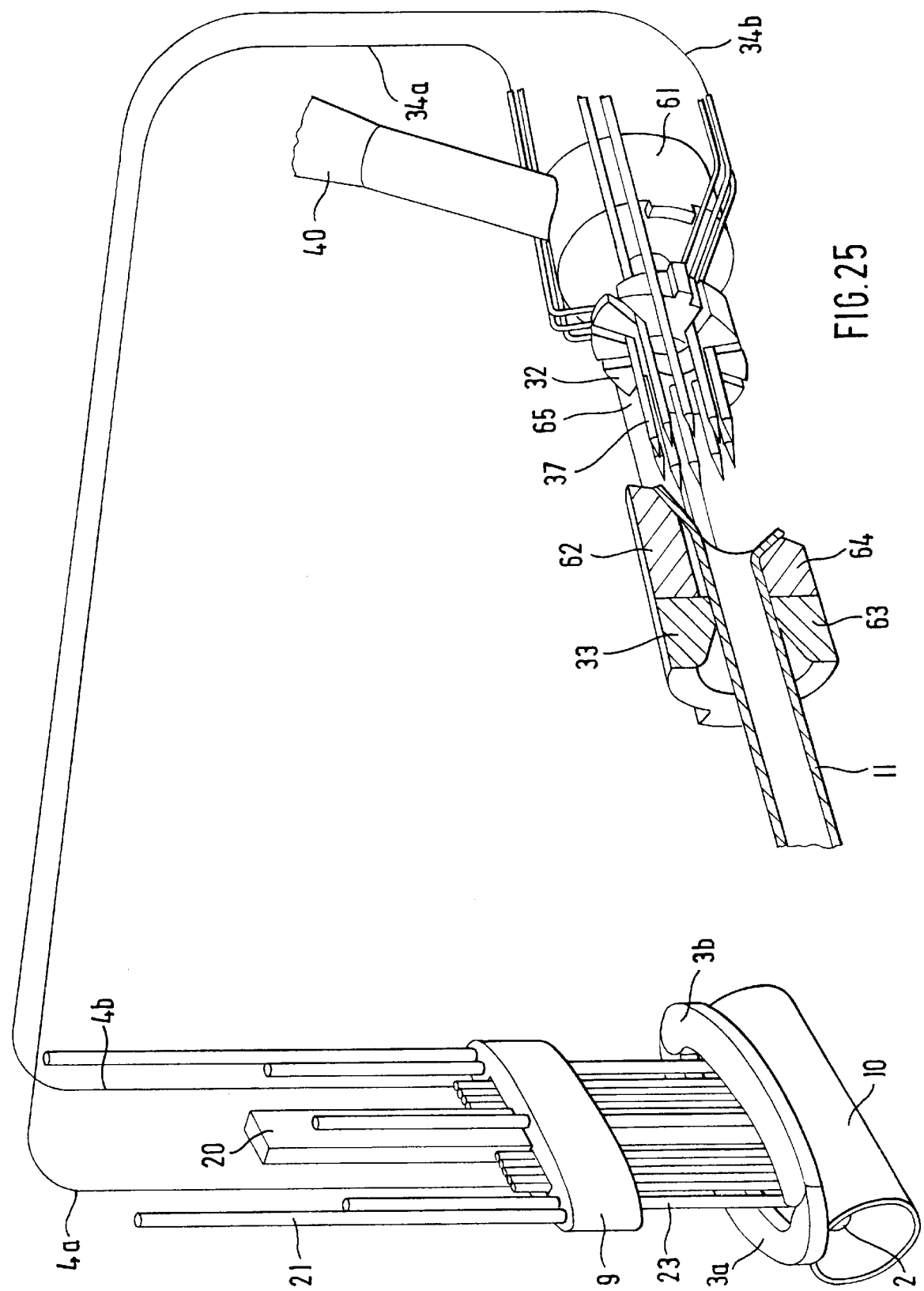
FIG. 25 shows the schematic of the set from FIG. 24 while the blood vessels are being sutured.

FIG. 25 shows this arrangement of the two devices according to the invention, the ends of whose needles are connected in each instance by sutures 4A, 34a or 4B, 34b.

Figure 26:
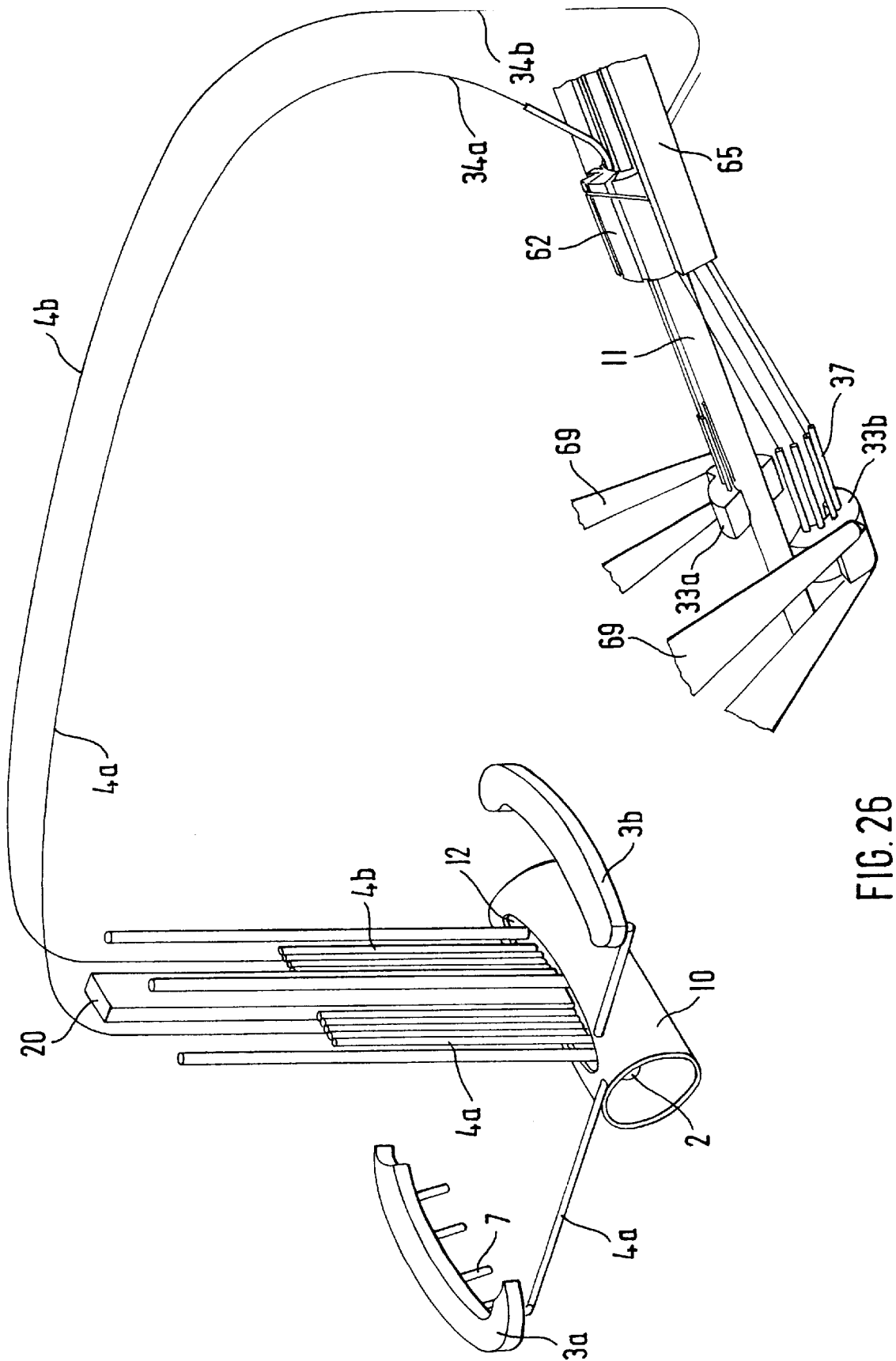
FIG. 26 shows an additional schematic of the set from FIG. 24 while the blood vessels are being sutured and FIGS. 27a–c show the sequence when suturing the transplant with a device in accordance with FIG. 23.

FIG. 26 shows the same arrangement after the needles 7 or 37 have been pulled through the artery 10 or the transplant 11. The needles 7 or 37 are then pushed into the needle seats 3 or 33 respectively and held in position there. The needle seats are now separated into two needle seat halves 3a, 3b or 33a and 33b respectively and removed with forceps 69 whose ends are adapted to the seat. Then the needle seats 3a, 3b, 33a, 33b can be set down in suitable seat cradles, and by pulling the sutures tight the transplant can be attached to the artery and thus sutured to it.

FIG. 27 shows in the subillustrations A through I the exact sequence of suturing the transplant. Here a device in accordance with FIG. 23 is used, where the same reference numerals are used for the same elements. FIG. 27A shows the device immediately prior to the suturing process. FIG. 27B shows how the transplant 11 is introduced into the needle seat 33 and the seat 62. FIG. 27C shows the transplant being held by suction against the inner walls of the passage of seats 33 and 62. In step 27D the transplant is cut off using a knife 66 along the diagonal surface 67 of the seat 62, so that it already has a diagonal aspect which matches the opening in the artery to which the transplant is to be sutured. In FIG. 27E the transplant 11 is being constricted behind its opening and the cutting surface 67 by means of pressure pads in the seats 33 and 62.

Figure 27A:
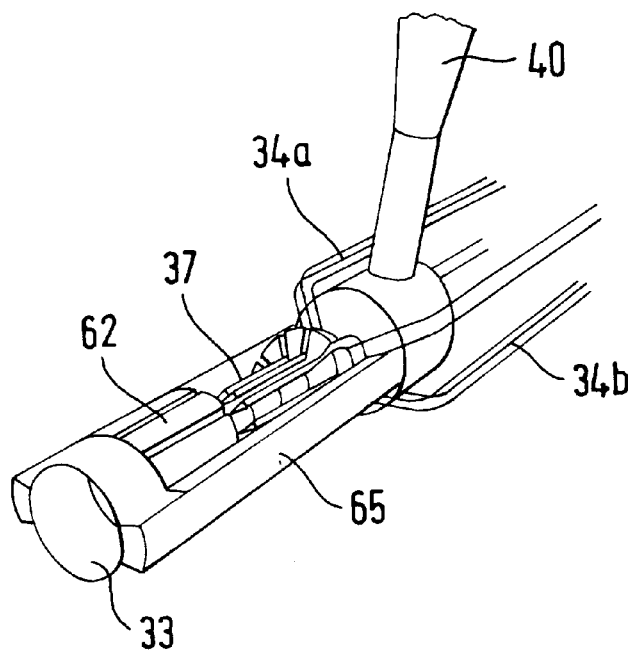
Figure 27B:
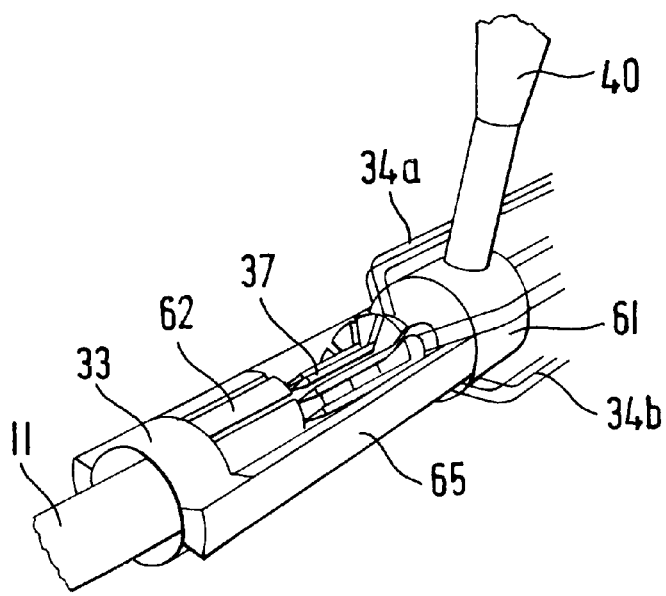
Figure 27C:
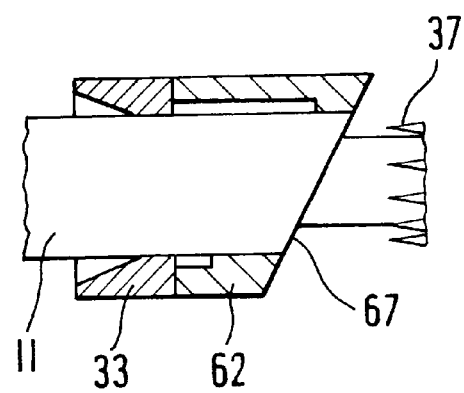
Figure 27D:
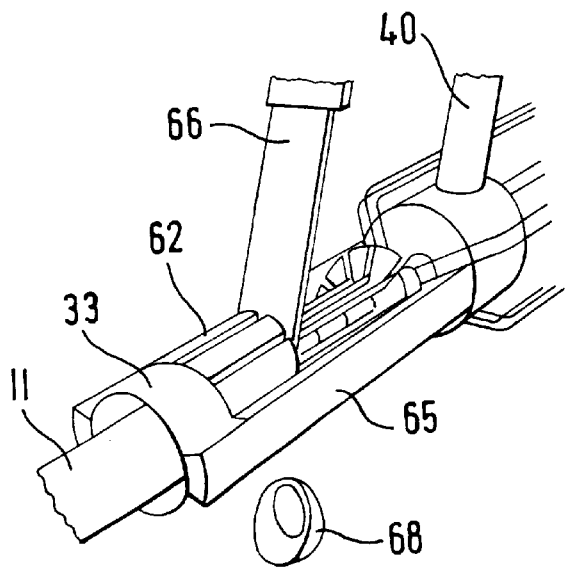
Figure 27E:
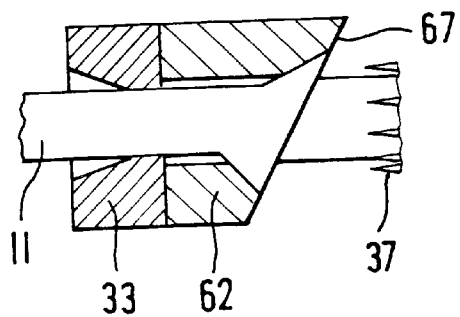
Figure 27F:
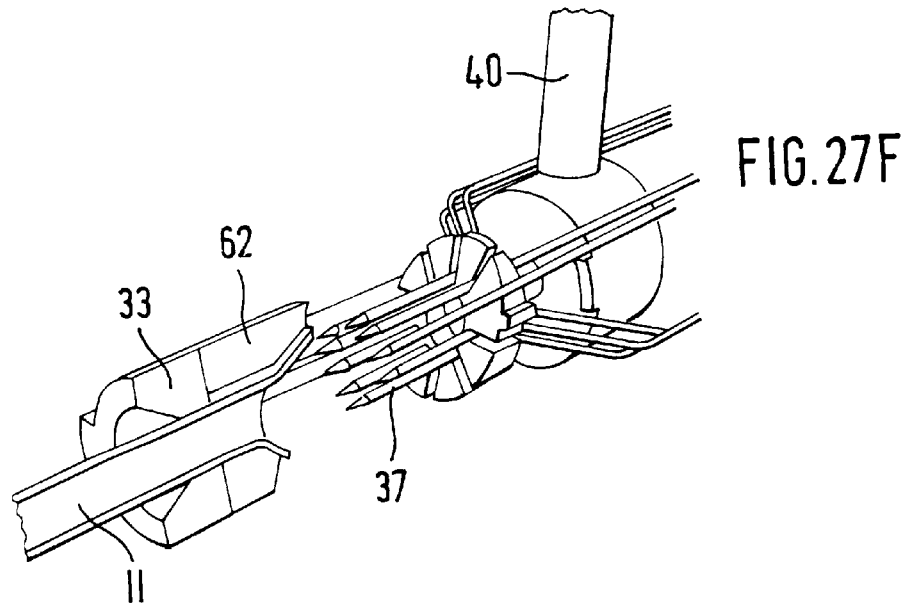

FIG. 27F shows how the needle array 37 is now displaced in an axial direction and thereby the individual needles 37 are pushed through the transplant 11 from the inside to the outside in the funnel-shaped constricted area.

FIG. 27G shows how, after the needles have been passed through the transplant, the needle seat 37 is withdrawn in an axial direction over the transplant and is then separated, and the two parts of the seat 33a and 33b are removed from the transplant.

FIG. 27H shows a cradle 41 for the needle seats 33a and 33b, while FIG. 27I shows how the needle seat 33b is placed in the cradle in such a way that one suture 34 is deposited in each of the slits 42 of the cradle 41.

The remainder of the process of attachment is performed as described in the previous examples.

In a further example, the instruments and devices presented could be designed as minimally invasive surgical instruments, so that it is not necessary to open the chest wall and the instrument is introduced into the body through small incisions, for example using a trocar.

In additional examples the handles 1 can also be designed in such a way that they can be manipulated by a robot. In this way, extensive automation of the suturing procedure would be possible.

In summary, it can be said that through the device under the invention, or through sets under the invention having two or more of such devices, at least one in each case for the artery side and one for the vein side, it is possible to join hollow organs together in a simple and safe manner.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. Device comprising:
   a lengthy holder for joining hollow organs or for closing blood vessels,
   a needle carrier, located at one end of the holder, wherein a needle seat forming an overhanging projection projects radially beyond the periphery of the holder and wherein a sleeve with a passage extending in the axial direction of the needles is located adjacent to the holder and above the needle points, the internal diameter of which is greater than the diameter of the needle array, and wherein the sleeve possesses elements in the area facing away from the needle points to constrict its passage.

2. Device in accordance with claim 1, wherein the device to deploy the needles is at a predetermined angle to the axial direction of the holder in a radial direction.

3. Device in accordance with claim 2, wherein the device for deploying the needles in a radial direction is an expanding sleeve which surrounds the holder and is movable in such a way between the needles and the holder that the needles are inclined outwards.

4. Device in accordance with claim 1, wherein adjacent to the holder and above the points of the needles an insertion aid is located for one of the hollow organs to be joined, extending radially beyond the particular needle adjacent to it or expandable in such a way that it extends radially beyond the particular needle adjacent to it.

5. Device in accordance with claim 1, wherein the elements to restrict the passages of the sleeve are inflatable pressure cushions.

6. Device in accordance with claim 1, wherein the sleeve possesses a device to generate a vacuum at its inner wall.

7. Device in accordance with claim 1, wherein an annular device to generate a vacuum is provided in the axial direction of the needles above the needle points.

8. Device in accordance with claim 7, wherein the device for generating a vacuum is formed annularly around the axial direction of the holder.

9. Device in accordance with claim 1, wherein the insertion aid or the sheath has radial notches or holes aligned in a straight line with the individual needles to permit passage of the individual needles.

10. Device in accordance with claim 1, wherein a needle cap covers the needles detachably.

11. Device under claim 10, wherein at least one of the needle cap and the needle seat can be at least one of separated and opened up along its periphery.

12. Device in accordance with claim 11, wherein at least one of the needle cap and the needle seat is can be divided into two parts along its periphery.

13. Device in accordance with claim 1, wherein the needle seat is positionable above the needle points and surrounding the holder, wherein said needle seat can be pushed onto the needle points or onto which the needle points can be pushed.

14. Device in accordance with claim 1, further comprises a retraction device to remove the needle cap from at least one of the needles and a motion device to move the expanding sleeve between the needles and at least one of the holder a pressure device to press the needle seat onto the needle points or the needle points onto the needle seat.

15. Device in accordance with claim 14, wherein the holder has controls to move at least one of the retraction device, the motion device and the pressure device.

16. Device in accordance with claim 15, wherein the controls have push buttons which are located at the opposite end of the handle to the needle carrier.

17. Device in accordance with claim 1, wherein a foot is located on the holder below the shoe.

18. Device in accordance with claim 1, further comprising a separate needle seat cradle for one or two needle seats.

19. Device in accordance with claim 1, further comprising a separate connecting device for attaching the ends of a suture.

20. Device in accordance with claim 1, wherein specific ends of a suture can be joined by means of a clip using the connecting device.

21. Set with at least two devices in accordance with claim 1.

22. Set in accordance with claim 21, characterized in that in each case one end of a needle of one device is connected by a suture with one end of a needle of the other device.

23. Procedure to join a first opening in a hollow organ with a second opening in a second hollow organ, comprising the steps of:

inserting a first array of needles into the first opening, inserting a second array of needles with the ends of the needles in front into the second opening, where the end of each needle in the first array is connected to the end of a needle in the second array by means of a suture, pushing the needles of each array jointly through the wall of the particular hollow organ along its opening with the needle points in front in each case, and subsequently pulling tight the sutures and tying the two ends of each suture together.

24. Procedure in accordance with claim 23, characterized in that the needles of one or both arrays are disposed in a ring.

25. Procedure in accordance with claim 23, characterized in that the needles of at least one of the arrays, after being inserted into the opening of the hollow organ, are splayed out from each other with their points in a radial direction.

26. Procedure in accordance with claim 23, characterized in that the opening of at least one hollow organ is expanded such that the hollow organ can be slipped over one of the arrays of needles with the area surrounding the opening, or one of the arrays of needles can be pushed through the area of the hollow organ surrounding the opening with a movement in the axial direction.

27. Procedure in accordance with claim 23, wherein the area of the hollow organ facing away from the opening of at least one hollow organ is constricted in such a way that the hollow organ can be slipped over one of the arrays of needles with the area surrounding the opening, or one of the arrays of needles can be pushed through the area of the hollow organ surrounding the with a movement in the axial direction.

28. Procedure in accordance with claim 27, wherein the area facing away from the opening is compressed.

29. Procedure in accordance with claim 23, wherein the hollow organ is pulled by vacuum against the inner wall of a sheath and held in position there.

30. Procedure in accordance with claim 23, characterized in that in order to push the needle points of at least one array through the wall of the hollow organ, a needle seat is pressed against the wall and at least one of the needle points on the side opposite the needle points, and the needle points are pushed against the wall and into a needle seat located on the opposite side to the needle points.

31. Procedure in accordance with claim 23, characterized in that the needle seat is pushed onto the needle points, or the needle points are pushed onto the needle seat, and the needle seat is then pulled away from the wall of the hollow organ.

32. Procedure in accordance with claim 23, characterized in that in conclusion the ends of the sutures are detached from the needles and attached, for example, knotted, clipped, bonded or laser welded.

* * * * *